(12) United States Patent
Eto et al.

(10) Patent No.: US 6,436,032 B1
(45) Date of Patent: Aug. 20, 2002

(54) DATA FILING SYSTEM FOR ENDOSCOPE

(75) Inventors: Tadao Eto, Hino; Hiroyuki Shibata, Yokohama; Hiroko Ohishi; Shinichi Omori, both of Hachioji; Keiichi Hiyama, Hino; Tatsuya Shiobara, Hachioji; Kazunori Matsuura, Tama, all of (JP)

(73) Assignee: Olympus Optical Co., Ltd. (JP)

( * ) Notice: Subject to any disclaimer, the term of this patent is extended or adjusted under 35 U.S.C. 154(b) by 222 days.

(21) Appl. No.: 09/580,727

(22) Filed: May 30, 2000

(51) Int. Cl.$^7$ ................................................ A61B 1/04
(52) U.S. Cl. ...................................... 600/117; 600/133
(58) Field of Search ................................. 600/117, 118, 600/133; 348/72, 74, 75

(56) References Cited

U.S. PATENT DOCUMENTS

| | | | | |
|---|---|---|---|---|
| 4,862,872 A | * | 9/1989 | Yabe et al. ................. | 600/133 |
| 4,996,975 A | * | 3/1991 | Nakamura ................... | 348/74 |
| 5,209,220 A | | 5/1993 | Hiyama et al. | |
| 5,830,121 A | * | 11/1998 | Enomoto et al. ........... | 600/117 |
| 5,871,439 A | * | 2/1999 | Takahashi et al. ............ | 348/74 |
| 5,967,969 A | * | 10/1999 | Enomoto et al. ........... | 600/117 |
| 6,313,868 B1 | * | 11/2001 | D'Alfonso et al. .......... | 348/72 |
| 6,331,181 B1 | * | 12/2001 | Tierney et al. .............. | 600/429 |
| 6,364,827 B1 | * | 4/2002 | Irion et al. ................. | 600/117 |

FOREIGN PATENT DOCUMENTS

JP   3-121038   5/1991

* cited by examiner

Primary Examiner—John P. Leubecker
(74) Attorney, Agent, or Firm—Ostrolenk, Faber, Gerb & Soffen, LLP

(57) ABSTRACT

Each of a plurality of endoscopes of an endoscope system is provided with a non-volatile memory in which information inherent to an endoscope, such as the model and manufacturing number, is stored. By a large capacity memory device provided in a server, which is connected with the endoscope through a network, with information inherent to each endoscope, the use condition, the cleaning condition, the cleaning effective period and the like are centrally administrated. Accordingly, the use condition, the cleaning condition and the like of each endoscope used in an endoscopic examination can be confirmed so that the endoscopic examination can be performed smoothly.

25 Claims, 19 Drawing Sheets

FIG.9A

| MODEL NAME | MANUFACTURING NUMBER | MANUFACTURING DATE | PURCHASE DATE |
|---|---|---|---|
| G-300 | 123-45 | 1998/9/7 | 1999/3/26 |
| REPAIR EXECUTION DATE ① | REPAIR POINT ① | REPAIR EXECUTION DATE ② | REPAIR POINT ② |
| YEAR, MONTH, DAY | | YEAR, MONTH, DAY | |

FIG.9B

| No | MODEL NAME | FACILITY NAME | USE START DATE |
|---|---|---|---|
| 1 | G-250 | YAMADA HP | 1998/5/21 |
| | FINAL USE DATE | EXAMINATION FREQUENCY | |
| | 1999/2/10 | 510 | |

FIG.10

| No | MODEL NAME | MANUFACTURING NUMBER | APPLICATION SITE | | NAME OF DOCTOR WHO USED DEVICE |
|---|---|---|---|---|---|
| 1 | G-250 | 000-11 | UPPER PORTION | GULLET,STOMACH | SATHO,ISHIDA |
| 2 | G-250 | 023-43 | UPPER PORTION | GULLET,STOMACH | SATHO,ISHIDA |
| 3 | G-300 | 012-35 | UPPER PORTION | GULLET,STOMACH,DUODENUM | SATHO,ISHIDA,OHTA |
| 4 | C-250 | 001-33 | LOWER PORTION | LARGE INTESTINE | YAMADA |
| 5 | C-250 | 002-22 | LOWER PORTION | LARGE INTESTINE | YAMADA |
| 6 | G-300 | 123-45 | UPPER PORTION | GULLET,STOMACH,DUODENUM | SATHO,ISHIDA,OHTA |

FIG.11

LIST OF EXAMINATION RESERVATION (1999/4/2)

| | 10:00 | 10:30 | ... | 14:00 |
|---|---|---|---|---|
| ENDOSCOPE SYSTEM 1-a | PATIENT ID : 000001<br>PATIENT NAME : ICHIRO TANAKA<br>UPPER PORTION | PATIENT ID : 000003<br>PATIENT NAME : HARUO YAMAMOTO<br>UPPER PORTION | ... | |
| ENDOSCOPE SYSTEM 1-b | PATIENT ID : 000015<br>PATIENT NAME : JIRO SUZUKI<br>UPPER PORTION,DOCTOR ISHIDA | PATIENT ID : 000048<br>PATIENT NAME : HANAKO UMEDA<br>UPPER PORTION | ... | |
| ENDOSCOPE SYSTEM 1-c | PATIENT ID : 002345<br>PATIENT NAME : SHIRO KAWASAKI<br>UPPER PORTION | | ... | PATIENT ID : 000001<br>PATIENT NAME : ICHIRO TANAKA<br>LOWER PORTION,DOCTOR YAMADA |

FIG.12

| No | MODEL NAME | MANUFACTURING NUMBER | FINAL USE DATE | FINAL CLEANING DATE | CLEANING EFFECTIVE PERIOD |
|---|---|---|---|---|---|
| 1 | G-250 | 000-11 | 1999/2/10 | 1999/3/18 | 60 DAYS |
| 2 | G-250 | 023-43 | 1999/3/25 | 1999/3/25 | 60 DAYS |
| 3 | G-300 | 012-35 | 1999/1/8 | 1999/1/9 | 60 DAYS |
| 4 | C-250 | 001-33 | 1999/2/2 | 1999/2/3 | 30 DAYS |
| 5 | C-250 | 002-22 | 1999/3/18 | 1999/3/11 | 30 DAYS |
| 6 | G-300 | 123-45 | | | 60 DAYS |

FIG.13

| No | MODEL NAME | MANUFACTURING NUMBER | USE START DATE | EXAMINATION FREQUENCY | EXTRACTION AND INSERTION FREQUENCY | RELEASE FREQUENCY | ACCUMULATED TIME-OF-USE |
|---|---|---|---|---|---|---|---|
| 1 | G-250 | 000-11 | 1998/5/21 | 510 | 598 | 21000 | 11670H |
| 2 | G-250 | 023-43 | 1998/5/25 | 435 | 502 | 17500 | 8380H |
| 3 | G-300 | 012-35 | 1998/6/1 | 256 | 265 | 49500 | 5610H |
| 4 | C-250 | 001-33 | 1998/7/10 | 57 | 81 | 955 | 310H |
| 5 | C-250 | 002-22 | 1998/9/11 | 135 | 195 | 1550 | 6240H |
| 6 | G-300 | 123-45 | 1999/4/2 | 0 | 0 | 0 | 0 |

FIG.14

| USE CONDITION OF ENDOSCOPE | | | |
|---|---|---|---|
| | No | MODEL | RECOMMENDATED MAINTENANCE TIME |
| ENDOSCOPE SYSTEM 1-a | 1 | G-250 | 1999/5 |
| ENDOSCOPE SYSTEM 1-b | 5 | G-250 | 1999/8 |
| ENDOSCOPE SYSTEM 1-c | 6 | G-300 | |
| CLEANING DEVICE | 3 | G-300 | 1999/12 |

FIG.15

| EXAMINATION RESULT REPORT (1999/4/2) | |
|---|---|
| PATIENT DATA<br>PATIENT ID : 000001<br>PATIENT NAME : ICHRO TANAKA<br>DATE OF BIRTH : 1956.2.10<br>AGE AT THE TIME<br>OF EXAMINATION : 44 | DETAIL OF EXAMINATION<br>EXAMINED PART : STOMACH<br>ENDOSCOPE USED : G-250<br>DOCTOR IN CHARGE<br>OF EXAMINATION : SATO<br>BIOPSY : ISHIDA |

FIG.16

| DISC No.1 RECORDED IMAGE | | | | |
|---|---|---|---|---|
| PATIENT ID | DESEASE NAME | BIOPSY | DOCTOR IN CHARGE OF EXAMINATION | USED ENDOSCOPE No. |
| 000001 | GASTRIC CANCER | | | |
| 000234 | | PRESENT | | |
| 001335 | | | SATO | 1 |
| ⋮ | ⋮ | ⋮ | ⋮ | ⋮ |

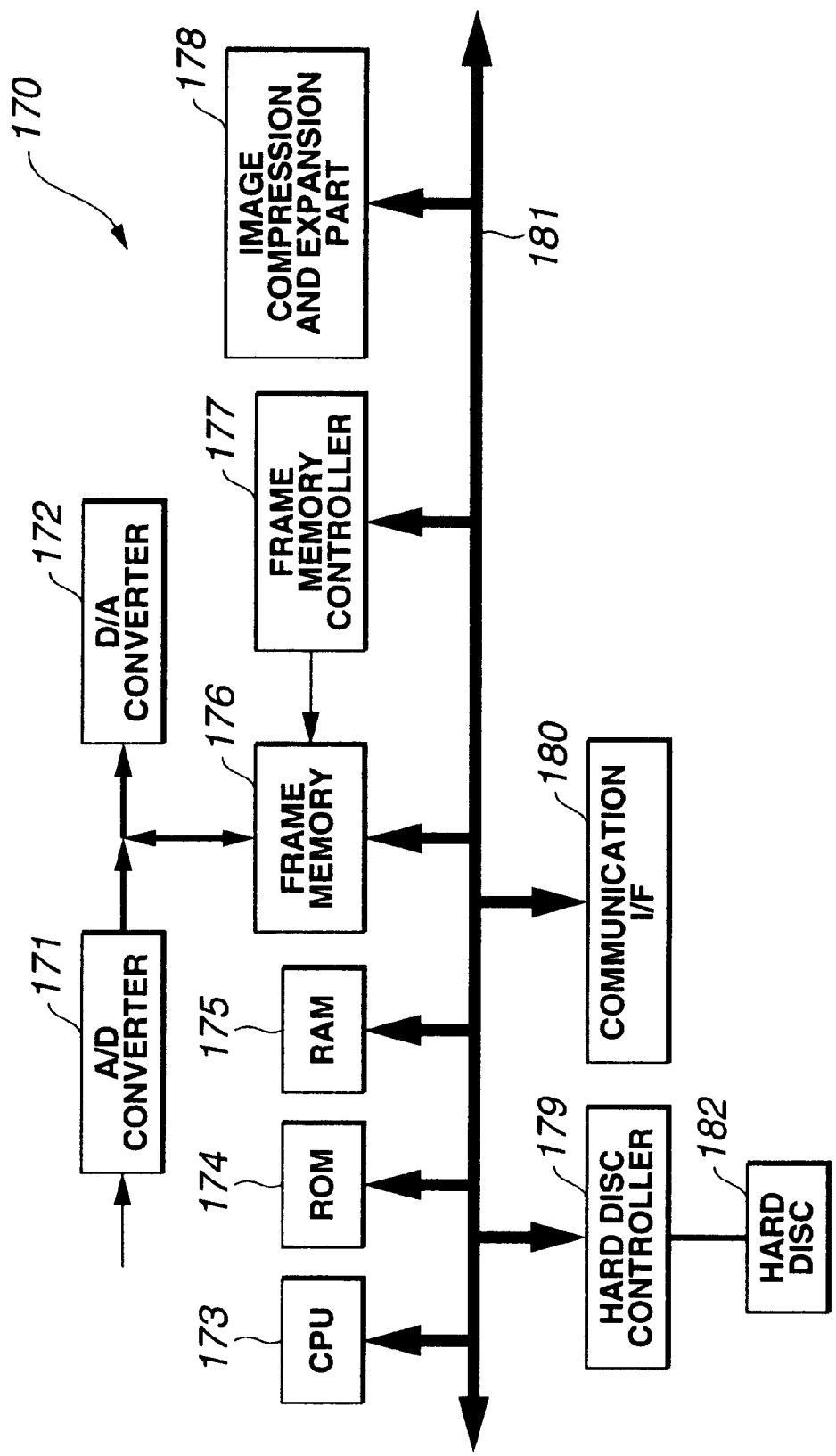

DATA FILING SYSTEM FOR ENDOSCOPE

This application claims benefit of Japanese Patent Application No. Hei 11-152267, filed in Japan, on May 31, 1999, and Japanese Patent Application No. Hei 12-122874, filed in Japan, on Apr. 24, 2000, the contents of which are incorporated herein.

BACKGROUND OF THE INVENTION

Field of the Invention and Related Art Statement

This invention relates to a data filing system for an endoscope which preserves endoscopic images and examination information in a recording medium, such as a network server, an optical disc or the like, and updates the images and the examination information preserved in the network server anytime.

Recently, a system which preserves medical images and examination information of an electronic endoscope in a recording medium, such as a server, and effectively employs them for subsequent diagnosis or the like has been adopted.

Japanese Laid-Open Patent Publication 121038/1991 proposes a technique which evaluates kinds of endoscopes in view of resistance held in the endoscopes and alters an image compression method for every kind of endoscope in view of an effective image range corresponding to the kind of the endoscope.

Although the above-mentioned image filing system may evaluate the kinds of endoscopes, the system cannot identify whether the endoscopes are of the same kind. Further, even if they may be identified, the use condition of these endoscopes for examination and whether they are clean cannot be confirmed.

SUMMARY OF THE INVENTION

It is an object of the present invention to provide a data filing system for an endoscope which can smoothly foster endoscopic examination by administrating the utilization and sanitary conditions thereof for examination for every endoscope.

It is another object of the present invention to provide a data filing system for an endoscope which assures easy administration of the endoscope.

According to the present invention, the data filing system for an endoscope comprises a plurality of endoscopes, identification information outputting devices disposed in respective endoscopes for outputting identification information necessary for identifying the respective endoscopes, an inherent information generating device for generating inherent information on operating conditions inherent to the respective endoscopes, and a memory device for storing endoscopic image data obtained through the respective endoscopes, the discrimination information outputted by the identification information outputting device and the inherent information generated by the inherent information generating device, while setting correspondence among these data and information, whereby the operating condition inherent to an endoscope can be ascertained for every endoscope with the identification information for identifying each endoscope, thus assuring a smooth operation of an endoscopic examination.

Further, according to the present invention, the data filing system for an endoscope comprises a plurality of endoscopes, identification information outputting devices disposed in respective endoscopes for outputting identification information necessary for identifying the respective endoscopes, an inherent information generating device for generating inherent information on sanitary conditions inherent to the respective endoscopes, and a memory device for storing endoscopic image data obtained through the respective endoscopes, the discrimination information outputted by the identification information outputting device and the inherent information generated by the inherent information generating device, while setting correspondence between these data and information, whereby information on the sanitary conditions inherent to an endoscope can be ascertained for every endoscope with the identification information for identifying each endoscope, thus assuring a smooth operation of an endoscopic examination.

Still further, according to the present invention, the data filing system for endoscope comprises a plurality of endoscopes, identification information outputting devices disposed in respective endoscopes for outputting identification information necessary for identifying the respective endoscopes, an inherent information generating device for generating inherent information on use frequency inherent to the respective endoscopes, and a memory device for storing endoscopic image data obtained through the respective endoscopes, the identification information outputted by the identification information outputting device and the inherent information generated by the inherent information generating device, while setting correspondence between these data and information, whereby information on the use frequency inherent to an endoscope can be ascertained for every endoscope with the identification information for identifying each endoscope, thus assuring a smooth operation of an endoscopic examination.

BRIEF DESCRIPTION OF THE DRAWINGS

The invention is described in detail below with reference to the following figures, throughout which similar reference characters denote corresponding features consistently, wherein:

FIG. 1 to FIG. 22 relate to the first embodiment of the present invention, wherein FIG. 1 is a schematic view of an image data filing system for an endoscope of the first embodiment, FIG. 2 is a schematic view of an endoscope system, FIG. 3 is a schematic view of an image recording and reproducing device, FIG. 4 is a schematic view of a server, FIG. 5 is a schematic view of an image recording device, FIG. 6 is a schematic view of an image reproducing device, FIG. 7 is a schematic view of an examination reservation device, FIG. 8 is a schematic view of an endoscope cleaning device, FIG. 9A and FIG. 9B are tables of inherent information preliminarily stored in EEPROMs of respective endoscopes and information to be stored in the EEPROMs by connecting the endoscope to an endoscope system, FIG. 10 is a table of the consent of an administration table of a large capacity hard disc of a server, FIG. 11 is a table of the examination reservation consent of an examination reservation device, FIG. 12 is a table of the consent of a sanitary condition administration table of a large capacity hard disc of a server, FIG. 13 is a table of the consent of an endoscope use condition administration table of a large capacity hard disc of a server, FIG. 14 is a display view of an endoscope use condition displayed on an examination reservation device, FIG. 15 is a display view of an examination report displayed by an image reproducing device, FIG. 16 is a display view of an examination designation table corresponding to a specific examination, FIG. 17 is a flow chart of a method for registering endoscope data at the time of completion of manufacturing of an endoscope, FIG. 18 is a flow chart of a method for describing information inherent to a non-volatile memory in an endoscope, FIG. 19 is a flow chart of a method for generating an endoscope administration table by describing endoscope data, FIG. 20 is a flow chart of a method for performing the confirmation of a sanitary condition of an endoscope, FIG. 21 is a flow chart of a method for administrating the use condition of an endoscope, and FIG. 22 is a schematic view of patient information data base stored while being correlated with an administration No. of an endoscope.

FIG. 23 and FIG. 24 relate to the second embodiment of the present invention, wherein FIG. 23 is a schematic view of an image data filing system for endoscope of the second embodiment, and FIG. 24 is a schematic view of a rental box.

DETAILED DESCRIPTION OF THE PREFERRED EMBODIMENTS

Figure 1:
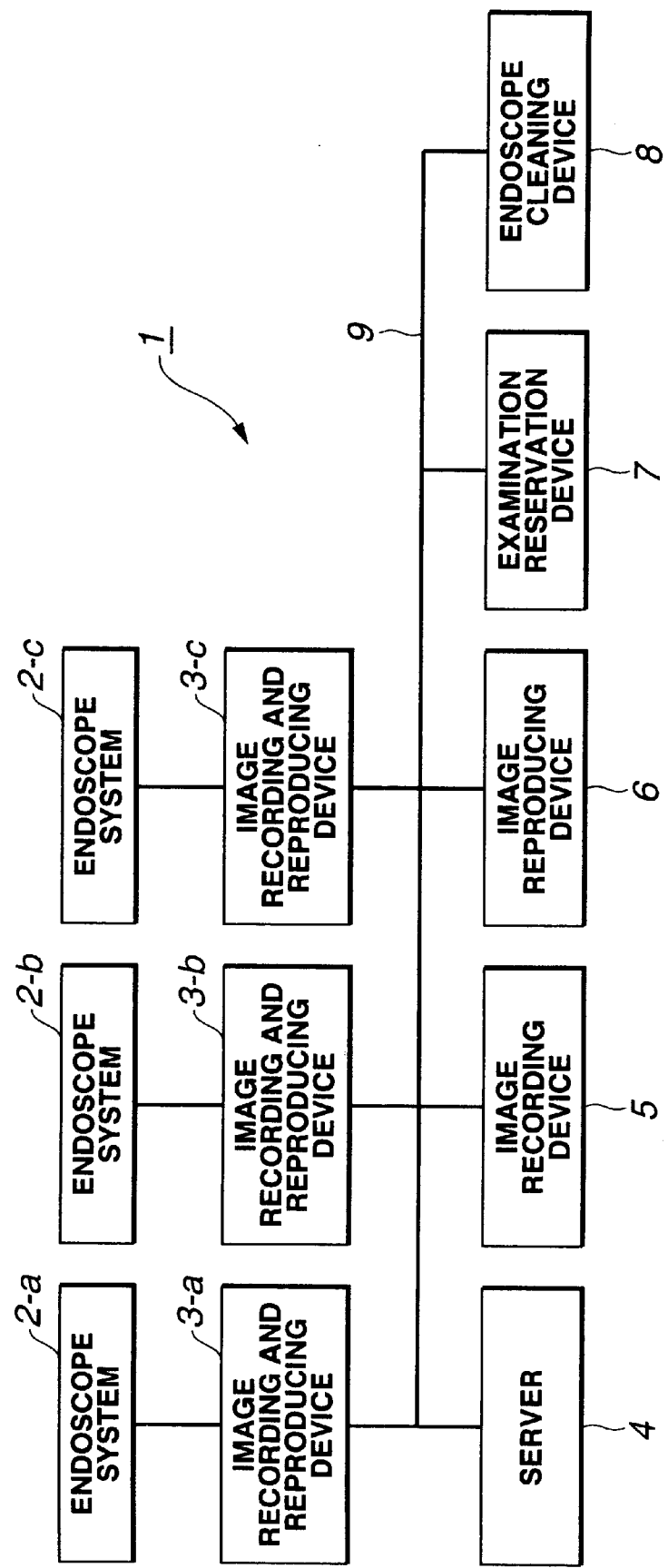

As shown in FIG. 1, an image data filing system 1 for an endoscope according to the first embodiment of the present invention is comprised of endoscope systems 2-*a*, 2-*b*, 2-*c*, image recording and reproducing devices 3-*a*, 3-*b*, 3-*c* respectively connected to the endoscope systems 2-*a*, 2-*b*, 2-*c*, a server 4, an image recording device 5, an image reproducing device 6, an examination reservation device 7 and an endoscope cleaning device 8, which are electronically connected with each other through a network 9.

Figure 2:
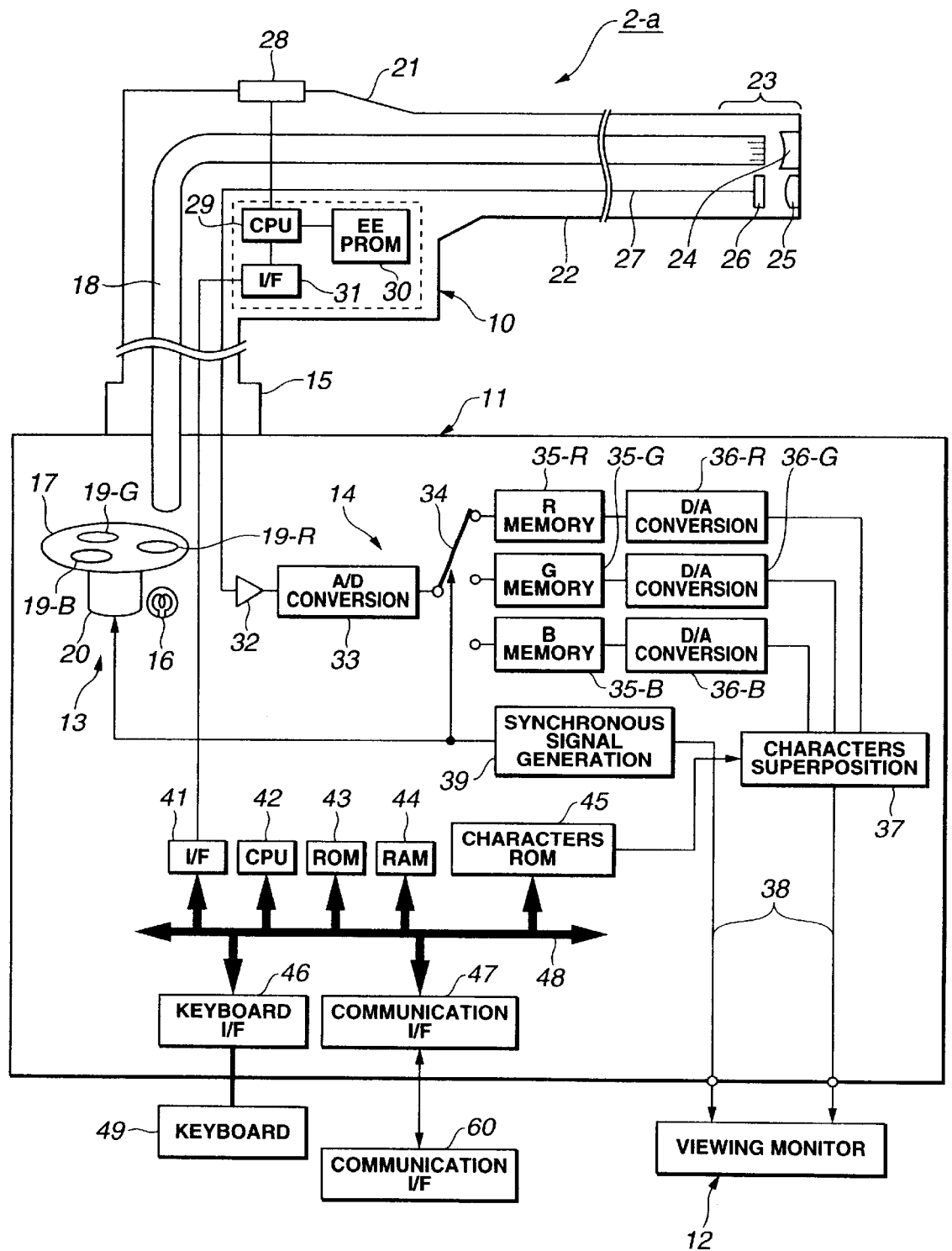

As shown in FIG. 2, the endoscope system 2-*a* is constituted by an endoscope 10, which is inserted into a body to be inspected, a video processor 11, which is connected to the endoscope 10 and performs signal processing and the like, and a viewing monitor 12, which displays a corresponding endoscopic image when video signals subjected to signal processing are inputted therein.

The video processor 11 includes a lighting source part 13 and a signal processing part 14. When a connector 15 of the endoscope 10 is connected to the video processor 11, the lighting source 13 supplies light to the endoscope 10.

A white light outputted from a lighting source lamp 16 disposed in the lighting source part 13 of the video processor 11 is inputted to a light guide 18 of the endoscope 10 through a face sequence filter 17 disposed in front of the lighting source lamp 16.

The face sequence filter 17 is provided with an R filter 19-R, a G filter 19-G and a B filter 19-B. By driving a filter drive part 20, such as a motor, the face sequence filter 17 is rotated at a constant speed. The filter disposed above an optical path opposite to the lighting source lamp 16 is changed over in sequence so that R, G, B light is sequentially inputted into the light guide 18. The light guide 18 has an end surface thereof disposed at a position which faces the lighting source lamp 16 in an opposed manner.

The light guide 18 of the endoscope 10 passes through a manipulation part 21 and the inside of a resilient insertion part 22, which is disposed at a front end of the manipulation part 21. The R, G, B light transmitted by the light guide 18 is irradiated from a lighting window of a distal portion 23 of the insertion part 22 through a lighting lens 24 and then to a viewing portion side, such as an affected part or the like, of the body to be inspected. The R, G, B light illuminates a viewing portion with sequential R, G and B lighting.

A viewing window is provided to a distal end portion 23 at a position close to the lighting window. An optical image of the viewing portion is formed at the image forming position by means of an objective lens 25 mounted on the viewing window. As a solid imaging element, for example, a CCD 26 is disposed at this image forming position. With the use of this CCD 26, the optical images formed under the sequential R, G and B light are converted to R, G and B imaging signals by a photoelectric conversion.

The CCD 26 is connected to the video processor 11 by means of a signal line 27. The R, G and B imaging signals are inputted to a signal processing part 14 of the video processor 11.

To the manipulation part 21 disposed at the rear end portion of the insertion part 22, which is inserted into a colon or the like, a release switch-28, which works as an instruction switch for performing a release action, is provided. This release switch 28 is, for example, connected to a CPU 29 incorporated in the manipulation part 21.

As a non-volatile memory which can be electrical rewritable, an EEPROM (electrically erasable programmable ROM) 30 is connected to the CPU 29. The EEPROM 30 is capable of writing and reading data.

Information inherent to the endoscope 10 is preliminarily written in the EEPROM 30 of every endoscope 10 in which the EEPROM 30 is incorporated (see FIG. 9A). By reading such information from the EEPROM 30, the EEPROM 30 forms means for generating identification information which enables the identification of the endoscope even when the kinds of endoscopes are the same kind (model). Inherent information on the inherent use condition of the endoscope 10 is stored in the EEPROM 30.

By reading and thereafter storing the inherent information to memory means while setting correspondence between the inherent information and the identification information, each endoscope can be centrally controlled or administrated.

An interface (hereinafter I/F) 31 is connected to the CPU 29. By connecting the connector 15 disposed at the rear end portion of the manipulation part 21 to the video processor 11, the I/F 31 is connected to of the video processor 11.

The signals subjected to photoelectric conversion by the CCD 26 are inputted to a buffer circuit 32, which constitutes a signal processing part 14 disposed in the inside of the video processor 11. Output signals of this buffer circuit 32 are inputted into an A/D converter 33. The R, G and B imaging signals (video signals) are converted to digital signals.

Output signals of the A/D converter 33 are inputted into a switching circuit 34 whereby the R video signals, G video signals and B video signals are respectively inputted into an R memory 35-R, a G memory 35-G and a B memory 35-B and are temporarily stored therein.

By reading and outputting the video signals temporarily stored in the R memory 35-R, the G memory 35-G and the B memory 35-B simultaneously at a given timing synchronized with a synchronous signal, simultaneous color image signals (standard video signals) are outputted.

The color image signals outputted from the R memory 35-R, the G memory 35-G and the B memory 35-B are converted to analogue signals by D/A converters 36-R, 36-G and 36-B. Thereafter, given characters information are added to the color image signals by a characters superposition circuit 37. Then, the color image signals are outputted to the viewing monitor 12 from an image output terminal (a video output terminal) through a cable 38. An operator can observe an endoscopic image displayed on the viewing monitor 12 and can perform a diagnosis and the like of a viewing portion such as a lesion or an affected part.

The video signals outputted from the video output terminal are also outputted to the image recording and reproducing device 3-a.

A synchronous signal generating circuit 39 is incorporated in the video processor 11 which transmits timing pulses necessary for driving the filter drive part 20. Change-over of the switching circuit 34 matches this timing, thus the R, G and B video signals are respectively inputted to the R memory 35-R, the G memory 35-G and the B memory 35-B. The synchronous signal from the synchronous signal generating circuit 39 is also outputted to the viewing monitor 12 at a synchronous signal output terminal of the video output terminal through the cable 38.

In the video processor 11, an I/F 41, a CPU 42, a ROM 43, a RAM 44, a characters ROM 45, a keyboard I/F 46 and a communication I/F 47 are disposed interconnected with each other by way of a bus 48.

The CPU 42 reads a program from the ROM 43 for controlling the video processor 11. The CPU 42 performs writing data to and reading data with from the RAP 44.

The I/F 41 disposed in the video processor 11 is connected to the I/F 31 disposed endoscope 10. The CPU 42 disposed in the video processor 11 performs the transmission end reception of control signals and data between the CPU 42 disposed in the video processor 11 and the CPU 29 disposed in the endoscope 10.

A keyboard 49 is connected to the keyboard I/F 46 for inputting of data and commands. The communication I/F 47 is connected to a communication I/F 60 of the image recording and reproducing device 3-a for transmission and reception of control signals and data.

The CPU 42 performs reading of the characters ROM 45 in response to control signals and data inputted or outputted between the keyboard 49 or the image recording and reproducing device 3-a and the CPU 42. The characters data read out from the characters ROM 45 are superposed on the RGB video signals at the characters superposition circuit 37 and are displayed on the viewing monitor 12.

Other endoscope systems 2-b, 2-c are similar to the endoscope 2-a hence, the explanation of same is omitted here.

Figure 3:
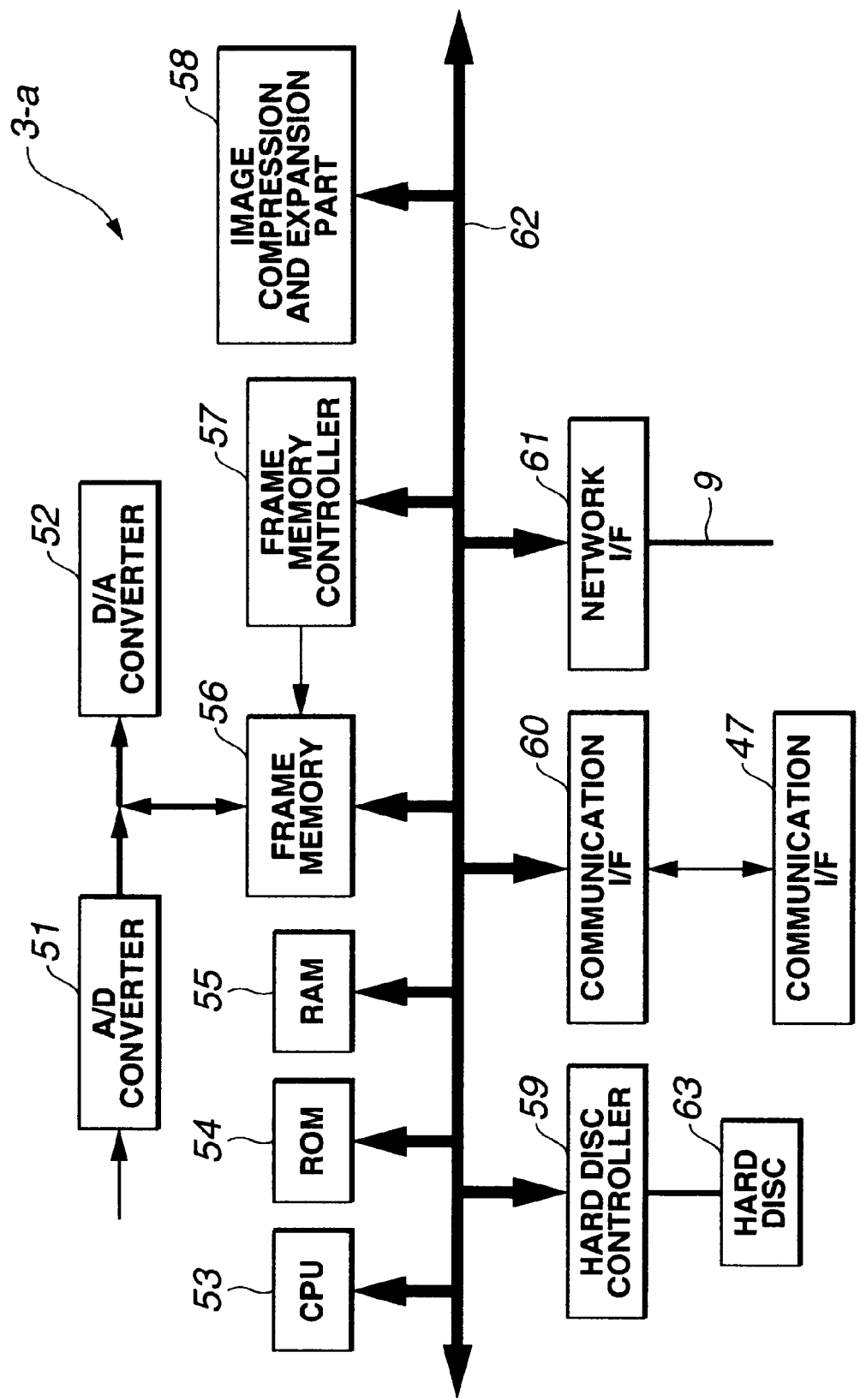

As shown in FIG. 3, in the image recording and reproducing device 3-a, the standard video signals transmitted from the video output terminal of the video processor 11 are inputted to an A/D converter 51 and converted to digital signals. These digital video signals are inputted to a D/A converter 52, converted to analogue signals and outputted thereafter.

The image recording and reproducing device 3-a further includes a CPU 53, a ROM 54, a RAM 55, a frame memory 56, a frame memory controller 57, an image compression and expansion part 58, a hard disc controller 59, a communication I/F 60 and a network I/F 61 which are connected with each other through a bus 62.

The CPU 53 reads a start-up program from the ROM 54 and performs a start-up control of the image recording and reproducing device 3-a. The CPU 53 performs writing data to and reading data from the RAM 55.

The A/D converter 51 is connected to the frame memory 56 so as to perform inputting of digital video signals. A control line from the frame memory controller 57 is connected to the frame memory 56, thus writing of digital video signals inputted from the A/D converter 51 is performed and, if necessary, the digital video signals are outputted to the D/A converter 52. The RGB video signals outputted from the frame memory 56 can be displayed as images on a viewing monitor (not shown).

With the frame memory controller 57, the digital video signals written in the frame memory 56 are transmitted to the image compression and expansion part 58 through the bus 62 so as to compress the image. The compressed video signals are temporarily stored in the RAM 55 as compressed image data and thereafter are recorded in the hard disc 63. The compressed video image may be outputted through the network I/F 61.

The compressed image data received by the network I/F 61 and the compressed image data recorded in the hard disc 63 are temporarily stored in the RAM 55 and thereafter are transmitted to the image compression and expansion part 58 where the image is expanded. The expanded data are stored in the frame memory 56 as digital video signals by the frame memory controller 57. The expanded data are outputted from the frame memory 56 to the D/A converter 52.

The hard disc 63 is connected to the hard disc controller 59. The CPU 53 reads a main program from the hard disc 63 and controls the image recording and reproducing device 3-a and the recording and reproducing of image data and the like.

The communication I/F 60 is connected to the communication I/F 47 of the video processor 11 so as to enable the transmission and reception of control signals and data.

The network I/F 61 is connected to the server 4, the image recording device 5, the image reproducing device 6, the examination reservation device 7 and the endoscope cleaning device 8 through the network 9.

The image recording and reproducing devices 3-b, 3-c are similar to the image recording and reproducing device 3-a thus, their explanation is omitted.

Figure 4:
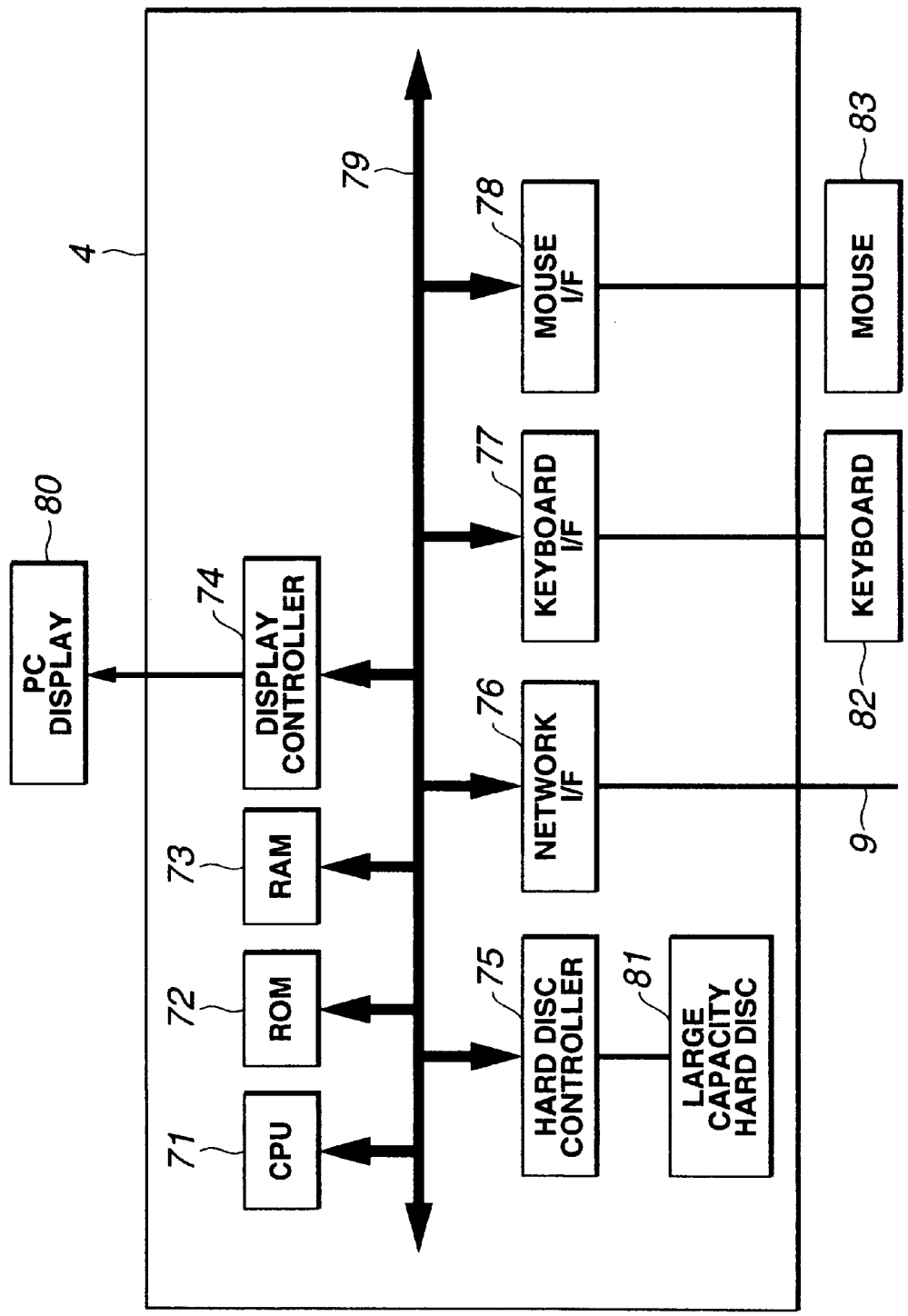

As shown in FIG. 4, in the server 4, a CPU 71, a ROM 72, a RAM 73, a display controller 74, a hard disc controller 75, a network I/F 76, a keyboard I/F 77 and a mouse 78 are interconnected through a bus 79.

The CPU 71 reads a start-up program from the ROM 72 and performs the start-up control of the server 4. The CPU 71 performs reading data from and writing data to the RAM 73.

A PC display 80 is connected to the display controller 74 to enable the display of data.

A large capacity hard disc 81 is connected to the hard disc controller 75. The CPU 71 performs reading of a main program from the large capacity hard disc 81 and performs control of the server 4 and the recording and reproducing of image data or the like.

The large capacity hard disc 81 stores administration information for centrally administering information regarding the endoscope of the endoscope system 2-*i* connected to the network 9 through the image recording device 3-*i*, where i=a–c. The information includes, for example, the use condition, the cleaning condition and whether the endoscope is capable of examining. Such information or the like correspond to inherent information of the endoscope, including the model of each endoscope 10. This allows the use condition or the like of each endoscope 10 to be easily confirmed thus assuring a smooth operation of the endoscope examination or the like.

The network I/F 76 is also connected to the image recording and reproducing devices 3-*a* to 3-*c*, the image recording device 5, the image reproducing device 6, the examination reservation device 7 and the endoscope clearing device 8 through the network 9.

A keyboard 82 is connected to the keyboard I/F 77. A mouse 83 is connected to the mouse I/F 78. Inputting of control commands and data is performed by means of the keyboard 82 and the mouse 83.

Figure 5:
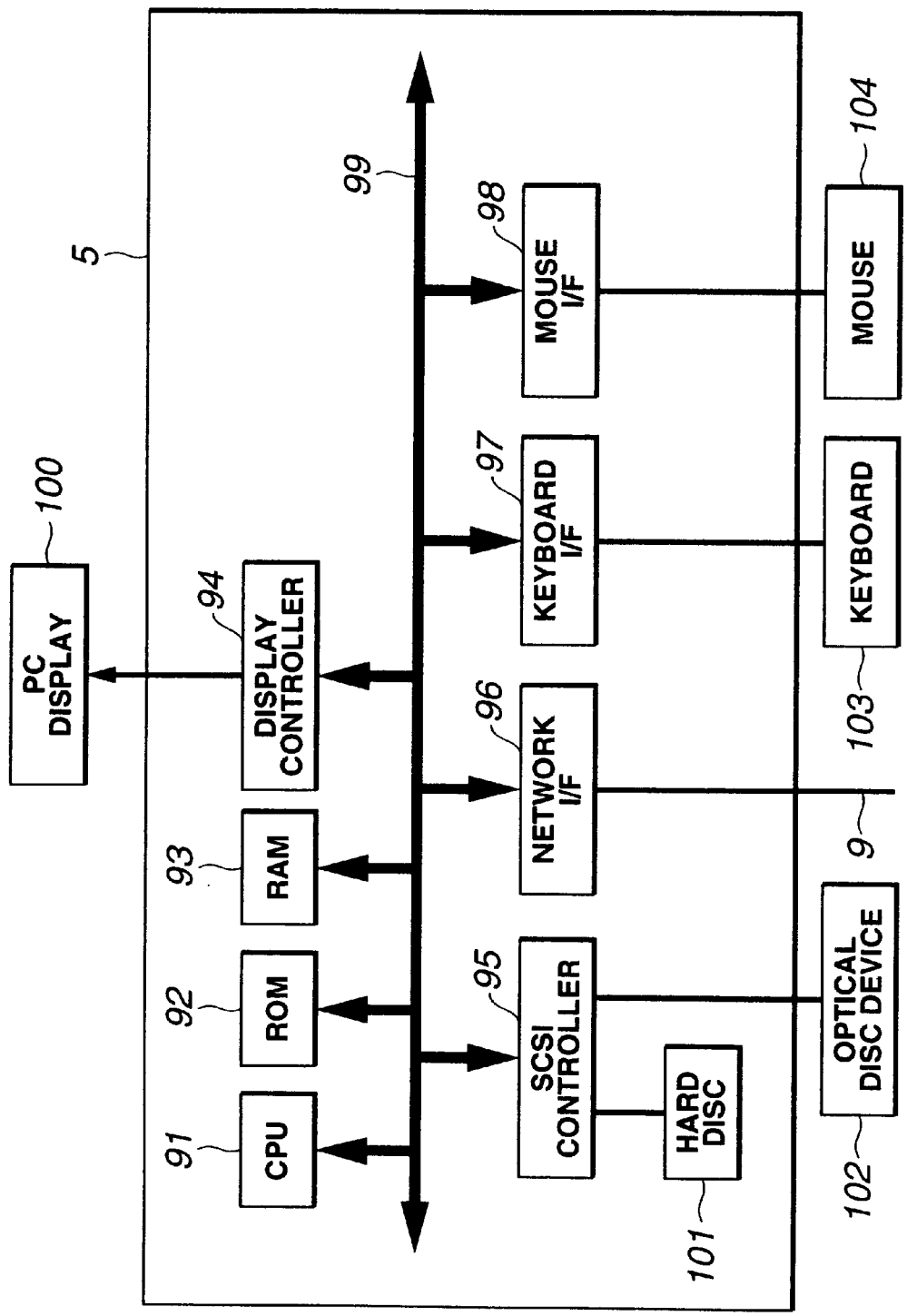

As shown in FIG. 5, in the image recording device 5, a CPU 91, a ROM 92, a RAM 93, a display controller 94, a SCSI controller 95, a network I/F 96, a keyboard I/F 97 and a mouse I/F 98 are interconnected through a bus 99.

The CPU 91 reads a start-up program from the ROM 92 and performs start-up control of the image recording device 5. The CPU 91 performs reading data from and writing data to the RAM 93.

A PC display 100 is connected to the display controller 94 so as to perform displaying of data.

A hard disc 101 and an optical disc device 102 are connected to the SCSI controller 95. The CPU 91 performs reading of a main program from the hard disc 101 and performs control of the image recording device 5. The CPU 91 performs recording image data onto and reproducing image data from the optical disc device 102.

The network I/F 96 is also connected to the image recording and reproducing devices 3-*a* to 3-*c*, the server 4, the image reproducing device 6, the examination reservation device 7 and the endoscope cleaning device 8 through the network 9.

A keyboard 103 is connected to the keyboard I/F 97. A mouse 104 is connected to the mouse I/F 98. Inputting of control commands and data is performed by manipulating the key board 103 or the mouse 104.

Figure 6:
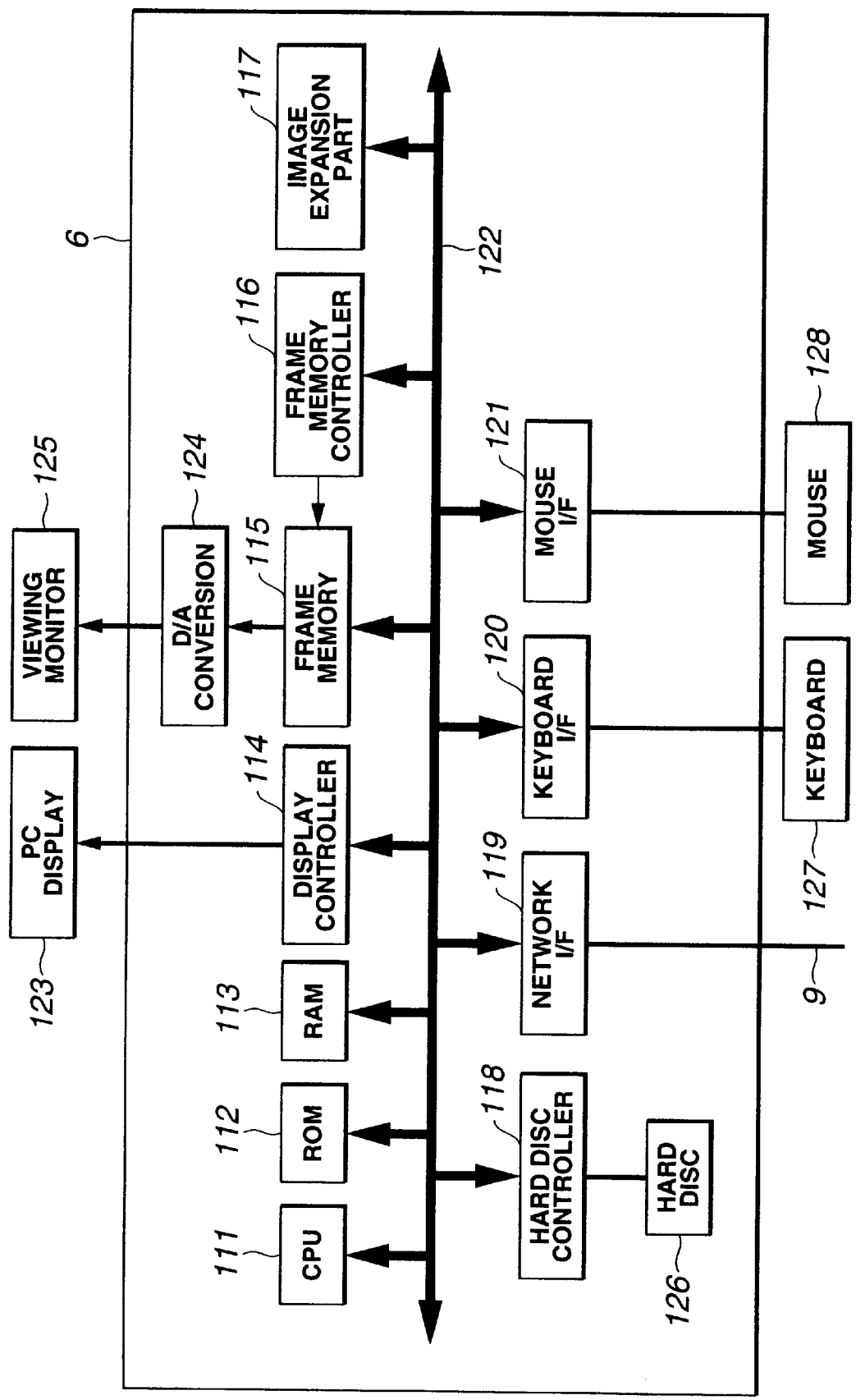

As shown in FIG. 6, in the image reproducing device 6, a CPU 111, a ROM 112, a RAM 113, a display controller 114, a frame memory 115, a frame memory controller 116, an image expansion part, 117, a hard disc controller 118, a network I/F 119, a keyboard I/F 120 and a mouse I/F 121 are interconnected through a bus 122.

The CPU 111 reads a start-up program from the ROM 112 and performs start-up control of the image reproducing device 6. The CPU 111 performs writing data to and reading data from the RAM 113.

A PC display 123 is connected to the display controller 114 so as to perform displaying of data.

Compressed image data received by the network I/F 119 are temporarily stored in the RAM 113 and thereafter are transmitted to the image expansion part 117 where the compressed image data are expanded. The frame memory controller 116 is connected to the frame memory 115. The expanded data are stored in the frame memory 115 as digital video signals with the control performed by the frame memory controller 116.

A D/A converter 124 is connected to the frame memory 115 to convert digital video signals to analogue video signals. A viewing monitor 125 is connected to the D/A converter 124. By outputting RGB video signals from the D/A converter 124 to the viewing monitor 125, the viewing monitor displays the RGB video signals.

A hard disc 126 is connected to the hard disc controller 118. The CPU 111 reads a main program from the hard disc 126 and performs control of the image recording device 5.

The network I/F 119 is connected to the image recording and reproducing devices 3-*a* to 3-*c*, the server 4, the image recording device 5, the examination reservation device 7 and the endoscope cleaning device 8 through the network 9.

A keyboard 127 is connected to the keyboard I/F 120. A mouse 128 is connected to the mouse I/F 121. Inputting of control commands and data is performed by manipulating the keyboard 127 or the mouse 128.

Figure 7:
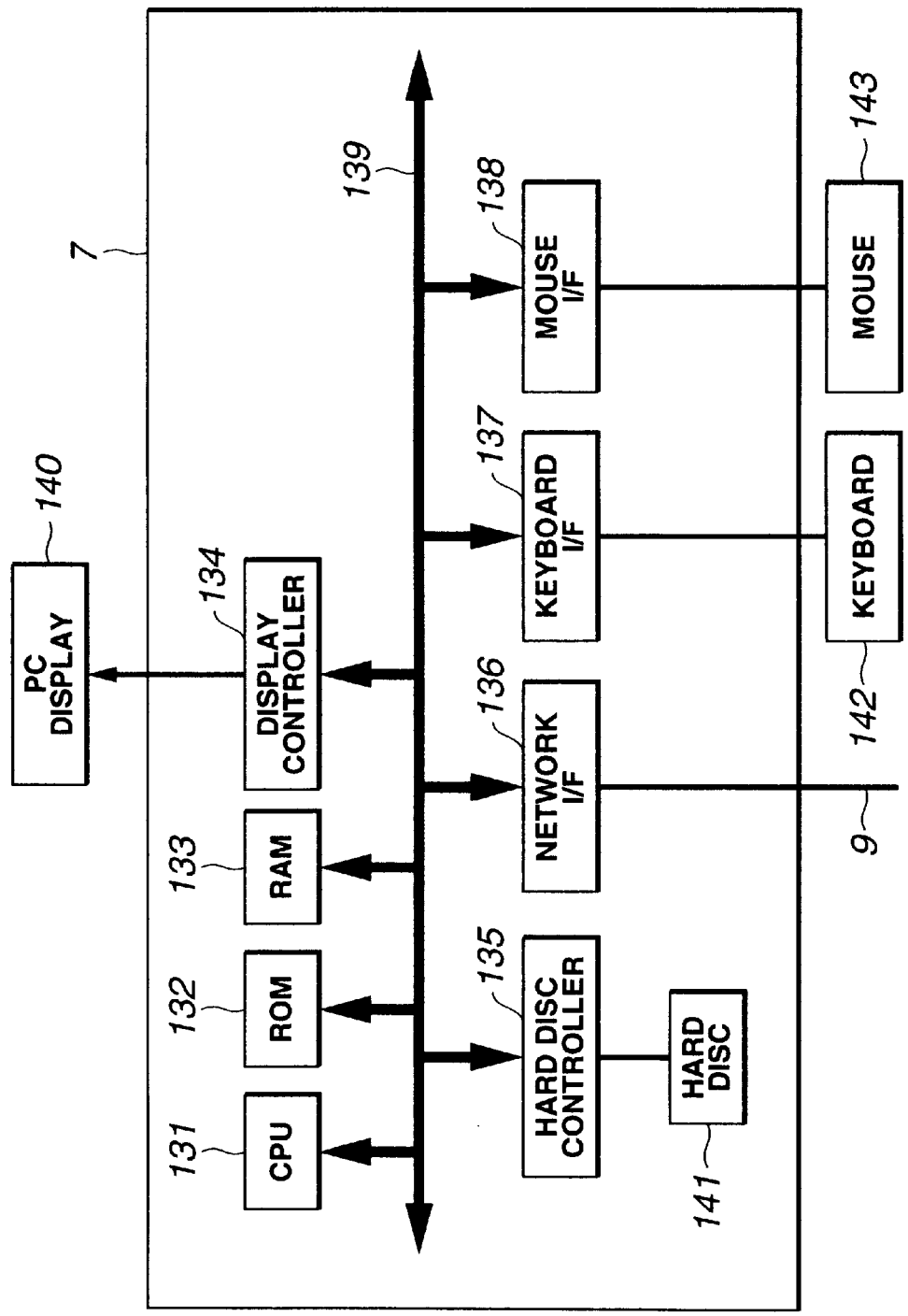

As shown in FIG. 7, in the examination reservation device 7, a CPU 131, a ROM 132, a RAM 133, a display controller 134, a hard disc controller 135, a network I/F 136, a keyboard I/F 137 and a mouse I/F 138 are interconnected through a bus 139.

The CPU 131 reads a start-up program from the ROM 132 and performs start-up control of the examination reservation device 7. The CPU 131 performs writing data to and reading data from the RAM 133.

A PC display 140 is connected to the display controller 134 so as to perform displaying of data.

A hard disc 141 is connected to the hard disc controller 135. The CPU 131 reads a main program from the hard disc 141 and performs control of the examination reservation device 7 as well as recording and reproducing of data.

The network I/F 136 is connected to the image recording and reproducing devices 3-*a* to 3-*c*, the server 4, the image recording device 5, the image reproducing device 6 and the endoscope cleaning device 8 through the network 9.

A keyboard 142 is connected to the keyboard I/F 137. A mouse 143 is connected to the mouse I/F 138. Inputting of control commands and data is performed by manipulating the keyboard 142 and the mouse 143.

Figure 8:
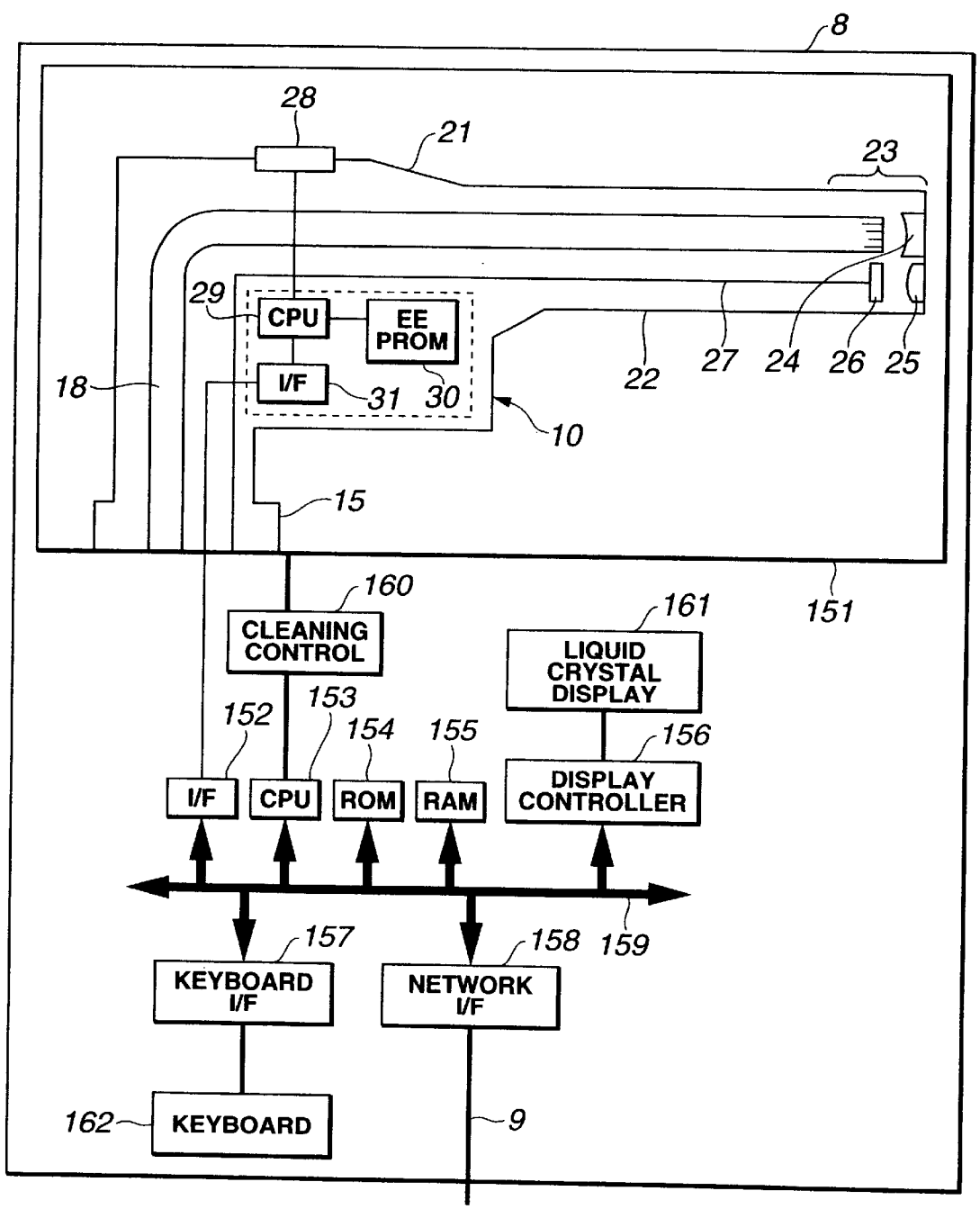

As shown in FIG. 8, the endoscope cleaning device 8 includes a cleaning vessel 151 in which the endoscope 10 can be accommodated.

The endoscope cleaning device 8 is provided with an I/F 152, a CPU 153, a ROM 154, a RAM 155, a display controller 150, a keyboard I/F 157 and a network I/F 158 which are interconnected through a bus 159.

The EEPROM 30 and the I/F 31 are connected to the CPU 29. By connecting the connector 15, which is provided to a rear end portion of the manipulation part 21, to the cleaning vessel 151, the I/F 31 is connected to the I/F152 of the endoscope cleaning device 8.

With such a constitution, the endoscope cleaning device 8 and the endoscope 10 perform the transmission and reception of control signals and data between the CPU 153 and the CPU 29 through the I/F 152 and the I/F 31.

The EEPROM 30 is connected to the CPU 29 which performs writing data to and reading data from the EEPROM 30.

The CPU 153 reads a program from the ROM 154 and performs control of the endoscope cleaning devices. The CPU 153 performs writing data to and reading data from the RAM 155.

A cleaning control part 160 is connected to the CPU 153. The cleaning vessel 151 is connected to the cleaning control part 160. The cleaning vessel 151 includes cleaning liquid supply means, cleaning liquid discharge means, endoscope drying means and the like (not shown). These are controlled based on the program read from the ROM 154.

A liquid crystal display 161 is connected to the display controller 156 so as to perform the displaying of data.

A keyboard 162 is connected to the keyboard I/F 157. Control commands and data are inputted by the keyboard 162.

The network I/F 158 is connected to the image recording and reproducing devices 3-a to 3-c, the server 4, the image recording device 5, the image reproducing device 6 and the examination reservation device 7 through the network 9.

In this embodiment, as will be explained in detail hereinafter, information on model names, manufacturing numbers and the like which constitute inherent identification information of each endoscope 10 are preliminarily written in the EEPROM 30 of each endoscope 10. Upon connecting the endoscope system 2-a, which connects each endoscope 10 to the video processor 11, to the server 4 through the image recording and reproducing device 3-a and the network 9, which is connected to the image recording and reproducing device 3-a, the server 4 generates an administration table. The server 4 writes and administrates inherent information of the endoscope 10 per se as well as inherent information on the use condition, such as the endoscope examination, while setting the correspondence between the former information and the latter information so as to centrally administrate each endoscope 10.

Inherent information on the cleaning of each endoscope 10 are centrally administrated by a cleaning condition administration table of the server 4 so that whether each endoscope 10 is available for examination can be confirmed. Inherent information or the like on the maintenance or the like is centrally administrated for every endoscope 10.

The manner of operation of this embodiment explained hereinafter.

The inherent information is preliminarily written in the EEPROM 30 disposed in for every endoscope 10.

One example is illustrated in a table shown In FIG. 9A.

Figure 17:
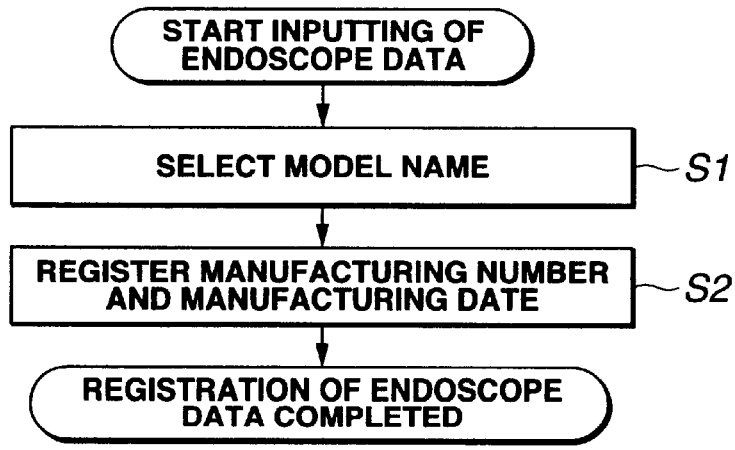

Processing for writing data into the EEPROM 30 upon completion of the manufacturing of the endoscope 10 is explained in conjunction with FIG. 9A and FIG. 17.

Writing of data into the EEPROM 30 is performed in the final step of manufacturing of the endoscope 10. Then the endoscope 10 is connected to the video processor 11 and is available for use. The user initiates a data input start-up by manipulating the keyboard 49 to start the inputting of data into the EEPROM 30.

Subsequently, in step S1, the registration of the endoscope models in the EEPROM 30 is performed. As shown in FIG. 1, the image recording and reproducing device 3-a is connected to the video processor 11. When the endoscope models are inputted by manipulating the keyboard 49, the inputted endoscope models are transmitted from the communication I/F 47 to the image recording and reproducing device 3-a. With the control performed by the hard disc controller 59, the inputted endoscope models are recorded in the hard disc 63. Accordingly, by preliminarily inputting the endoscope models by manipulating the keyboard 49, the endoscope models can be registered or recorded in the hard disc 63.

In step S1, data on a plurality of endoscope models, which are already registered, are transmitted to the video processor 11 from the communication I/F 60. The data on a plurality of endoscope models are superposed onto video signals in the characters superposition circuit 37 of the video processor 11 and displayed on the viewing monitor 12. The model corresponding to the endoscope is selected from a plurality of endoscope models. The selected endoscope model is transmitted to the endoscope 10 through the I/F 41 and is written in the EEPROM 30 as shown in the table 1 of FIG. 9A with the control performed by the CPU 29.

A model which is not registered in the hard disc 63 can be inputted by manipulating the keyboard 49 and written in the EEPROM 30. In this case, this model name can be transmitted to the image recording and reproducing device 3-a through the communication I/F 47 and can be recorded in the hard disc 63.

Subsequent to inputting of the model names, manufacturing dates and manufacturing numbers are registered in step S2. With respect to the manufacturing dates, the CPU 42 of the video processor 11 has a clock (not shown) and transmits acquired date from the I/F 41 to the endoscope 10 and writes the date in the EEPROM 30, as shown in the table 1 of FIG. 9A.

Manufacturing numbers are written in the hard disc 63 disposed in the image recording device 3-a for every manufacturing model together with manufacturing dates. Whether the same models are registered is confirmed. For example, if the last registered number of the same model is 123-44, as shown in the tablet of FIG. 9A, the I/F 41 adds 1 to 123-44 for 123-45, which is transmitted from the I/F 41 to the endoscope 10 as a new registered number and is written in the EEPROM 30. Following writing, the manufacturing date 1998/9/7 and the manufacturing number 123-45 are recorded in the hard disc 63 of the image recording device 3-a, completing the endoscope data registration processing of FIG. 17.

In case plural sets of endoscope systems 2-a to 2-c and plural sets of image recording and reproducing devices 3-a to 3-c are connected to the network 9 as shown in FIG. 1, the manufacturing models and the manufacturing numbers may be recorded in the large capacity hard disc 81 of the server 4 in place of the hard disc 63 and maybe read from the large capacity hard disc 81 in step S2 of FIG. 17.

FIG. 9B shows a case where the information inherent to the endoscope 10 is written in the EEPROM 30 disposed in the endoscope 10 of the endoscope system 2-a, which is connected to the endoscope image filing system 1 at the time of delivering the endoscope 10. The step for writing data in the EEPROM 30 is explained hereinafter in conjunction with FIG. 18.

When the endoscope 10 is connected to the video processor 11 of the endoscope system 2-a and the power source of the video processor 11 is turned on, whether the video processor 11 is communicable with the CPU 29 of the endoscope 10 through the I/F 41 is checked.

Figure 18:
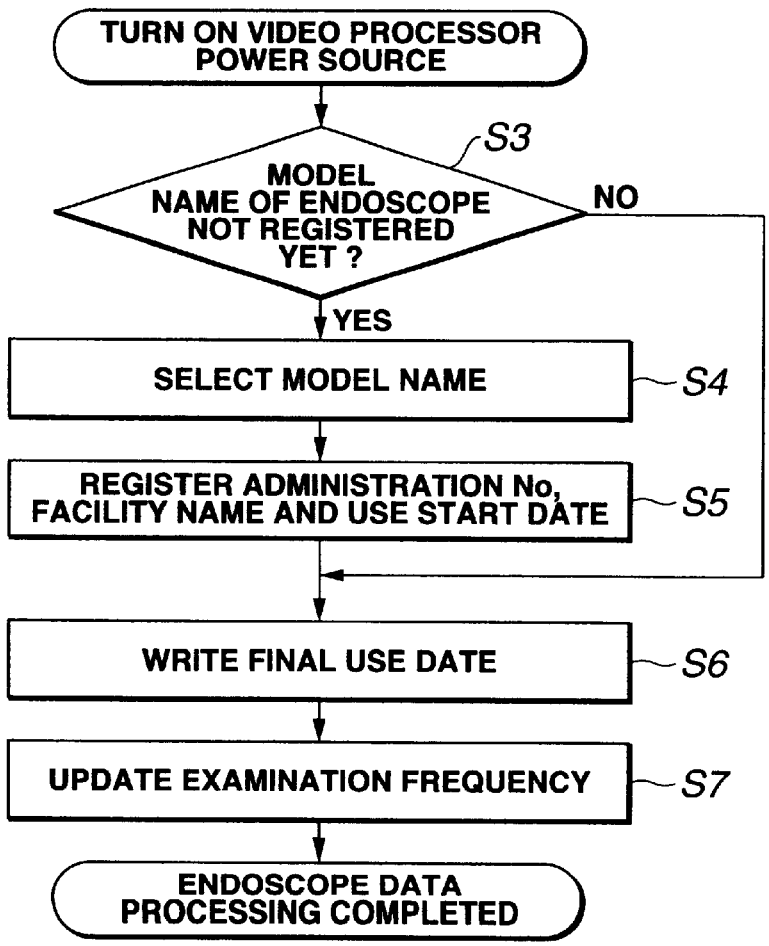

If the communication check reveals that the video processor 11 can communicate with the CPU 29, in a subsequent step S3 of FIG. 18, with respect to the data registration condition in the inside of the EEPROM 30, whether the endoscope model name is registered is confirmed with the control performed by the CPU 29.

Once data is registered in the EEPROM 30, the data is not corrected. In case the same endoscope 10 is connected to the video processor 11 and the power source is turned on again, since the CPU 29 determines whether the endoscope models are already registered in step S3, step S4 and step S5 are skipped and the processing advances from step S3 to step S6.

As a result of checking in step S3, if the endoscope model names are not yet registered, the processing advances to step S4 and writing of the endoscope model names is performed. Since the endoscope model names are recorded in the hard disc 63 of the image recording and reproducing device 3-*a*, the endoscope model names are read with the control performed by the hard disc controller 59. The read-out endoscope model names are superposed onto the video signals in the characters superposition circuit 37 and are displayed on the viewing monitor 12. Thus, the endoscope model name corresponding to the endoscope is selected with the manipulation of the keyboard 49. The endoscope model name may be inputted by manipulating the keyboard 49. The selected or inputted endoscope model name is written in the EEPROM 30.

Then, the processing advances to step S5 where the administration numbers are prepared for each manufacturing number of every endoscope to be administrated. The administration numbers, the facility names and the use start dates are registered.

The facility names are registered in the large capacity hard disc 81 of the server 4, transmitted from the network I/F 76 to the network I/F 61 and inputted into the image recording and reproducing device 3-*a*.Then, data on the facility names are further outputted from the communication I/F 60 together with the set administration numbers and transmitted to the video processor 11 through the communication I/F 47. Data on the administration numbers and the facility names are transmitted to the endoscope 10 through the I/F 41 and are written in the EEPROM 30 with the control performed by the CPU 29.

Subsequent to writing of the data on the administration numbers and the facility names into the EEPROM 30, the data on the use start dates are acquired from the date information administrated by the clock (not shown) provided to the CPU 71 of the server 4. As in the case of the data on the administration numbers and the facility names, the data on the use start dates are transferred from the server 4 to the endoscope 10 through the network I/F 76, the network I/F 61, the communication I/F 60, the communication I/F 47, the I/F 41 and the I/F 31 and are written in the EEPROM 30.

Subsequent to the completion of the processing of step S5, the processing of step S6 is performed.

In step S6, the processing waits for the entry of patient data by manipulating the keyboard 49 of the video processor 11.

In case the patient data is inputted in step S6, the CPU 71 determines whether the examination has started. After inputting the patient data, the time and date information administrated by the clock (not shown) provided to the CPU 71 of the server 4 is acquired from the server 4 through the network I/F 76, the network I/F 61, the communication I/F 60, the communication I/F 47, the I/F 41 and the I/F 31 and are written in the EEPROM 30 as the final use date.

When step S6 is completed, the processing advances to step S7. In step S7, with the control performed by the CPU 29, the number of examinations stored in the EEPROM 30 is read, one is added to the read-out number of examinations and the sum is written in the EEPROM 30 thus completing this processing.

Even when the endoscope 10 is mounted on the video processor 11, there may be a case that the patient data is not inputted, that is, the power source is turned off without performing the examination. In this case, the processing is stopped at step S6 and the final use date and the number of examinations are not updated.

Figure 19:
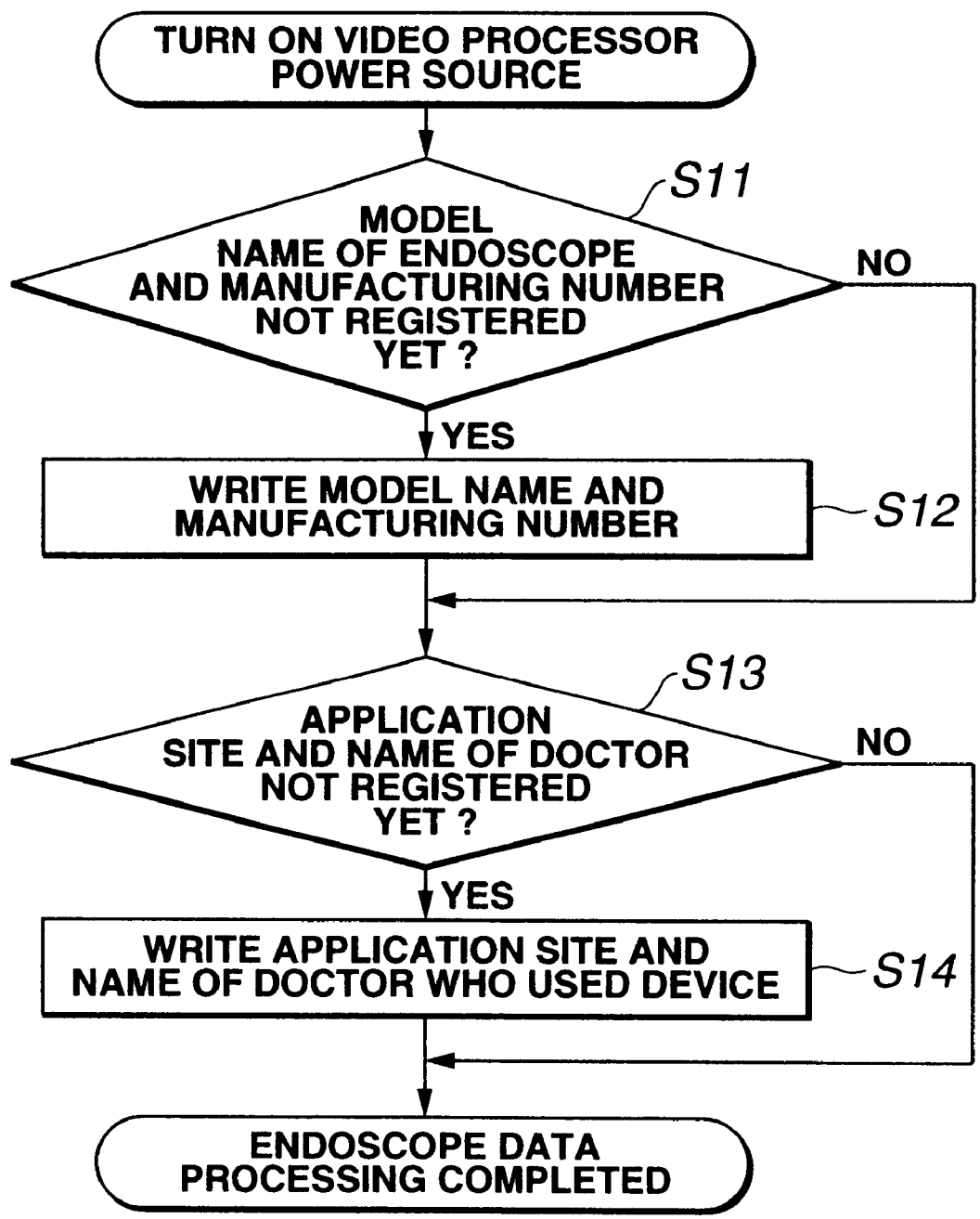

The endoscope administration table, which administers the endoscope 10 shown in FIG. 10, is recorded in the large capacity hard disc 81 of the server 4. Steps for writing the endoscope administration table are explained in conjunction with FIG. 19.

First, the endoscope 10 is connected to the video processor 11 of the endoscope system 2-*a* and the power source of the video processor 11 is turned on.

In step S11, the server 4 reads the file of the endoscope administration table from the large capacity hard disc 81 with the control performed by the CPU 71 and preserves the file on the RAM 73. Then, the CPU 71 determines whether the data of the endoscope 13 is present in the endoscope administration table, that is, whether the endoscope model names and the manufacturing numbers are unregistered.

Data shown in FIG. 9A are recorded in the EEPROM 30 of the endoscope 10 at the time of manufacturing.

With the control performed by the CPU 29, data on the model name "G-300" and the manufacturing number "123-45" are read from the EEPROM 30 of the endoscope 10. The read-out data on the model name and the manufacturing number are inputted to the video processor 11 through the I/F 41.

The data on the model names and the manufacturing numbers are transmitted to the image recording and reproducing device 3-*a* from the communication I/F 47. The image recording and reproducing device 3-*a* receives the data through the communication I/F 60 and transfers the data to the server 4 through the network I/F 61.

In the server 4, the CPU 29 confirms whether the combination of the model name "G-300" and the manufacturing number "123-45" is present in the endoscope administration table. Where the endoscope 10 is used for the flash time, the model name "G-300" and the manufacturing number "123-45" are not present in the endoscope administration table and hence, the processing advances to step S12.

When the combination of the model name and the manufacturing number of the endoscope 10 has been already registered in the endoscope administration table, the processing advances to step S13.

In step S12, the model name "G-300" and the manufacturing number "123-45" of the endoscope 10 which are received by the server 4 are respectively written in the endoscope administration table. Upon completion of writing, the data of the large capacity hard disc 81 are updated and the processing advances to step S13.

In step S13, the CPU 29 confirms whether the application site and the name of a doctor have been already registered in the endoscope administration table. Where they have been already registered, the processing is completed. Where they are not yet registered, the processing advances to step S14.

In step S14, the application site and the name of a doctor are written or registered in the endoscope administration table, i.e., the same model "G-300" with the endoscope 10 has been already registered, the same application site and the same doctor who uses the endoscope are applied to the model name "G-300", and the manufacturing number "123-45" and are written in the endoscope administration table. If the same model has not been registered, the application site and the name of the doctor who uses the endoscope are inputted and -written by manipulating the keyboard 49 of the video processor 11.

Upon completion of writing, presentation processing is performed, the data of the large capacity hard disc 8. is updated and processing is completed.

The administration table, shown in the table of FIG. 10, may be displayed on the PC display 127 of the lease reproducing device 6. Manipulation of the keyboard 127 or the mouse 128 enables editing of the application sites and the names of doctors who use endoscopes. If the same model as the newly registered endoscope 10*d* has been already registered, with respect to the application site and the name of the doctor who uses the endoscope, the same data as this model is automatically registered and hence, some modification may be performed if necessary.

Upon completion of the registration of the endoscope 10, examination reservation is performed by means of the examination reservation device 7 before carrying out examination.

One example of the examination reservation window displayed on the PC display 140 of the examination reservation device 7 is shown in FIG. 11.

As shown in FIG. 11, patient data, such as the patient ID, for example, are inputted into the examination reservation window by manipulating the keyboard 142 or the mouse 143 for every endoscope system. Taking into account when an upper portion and a lower portion are continuously subjected to examination with respect to the same patient, the kind of examination with respect to the upper portion or the lower portion, the name of doctor in charge of examination are inputted by manipulating the keyboard 142 or the mouse 143. The inputted data are added to the data base of the patient data read from the large capacity hard disc 81 of the server 4 and are recorded in the large capacity hard disc 81.

Before performing the examination, the confirmation of the sanitary condition of the endoscope 10 to be used is performed. The sanitary condition administration table of the sanitary condition of the endoscopes 10 is shown in FIG. 12.

The sanitary condition administration table is recorded in the large capacity hard disc 81 of the server 4.

Every time endoscopic examination or endoscope cleaning is performed, data on the final use day or that cleaning date are transmitted from the image recording and reproducing devices 3-*a* to 3-*c* or the endoscope cleaning device 8 to the server 4. Upon receiving these date, the server 4 updates the sanitary condition administration table and writes same in the large capacity hard disc 81.

On the last use day, after writing the last use day in the endoscope 10 in step S6 of FIG. 18, the sanitary condition administration table is read from the server 4 and recorded in the large capacity hard disc 81 based on the time information administrated by a clock (not shown) provided to the CPU 71.

After completion of an endoscopic examination, the endoscope 10 is mounted on the endoscope cleaning device 8 and cleaned. The cleaning is performed by controlling the cleaning control part 160 with the CPU 153. Upon completion of cleaning, a notification of completion of cleaning, the model and manufacturing number of the cleaned endoscope are outputted from the network I/F 158.

The notification of completion of cleaning outputted from the endoscope cleaning device 8, the endoscope model and the manufacturing number are inputted into the server 4 through the network I/F 76. Based on the model and the manufacturing number of the endoscopes corresponding to the time information administrated by a timer (not shown) provided to the CPU 71, the last cleaning day of the sanitary condition administration table is updated and recorded in the large capacity hard disc 81.

Figure 20:
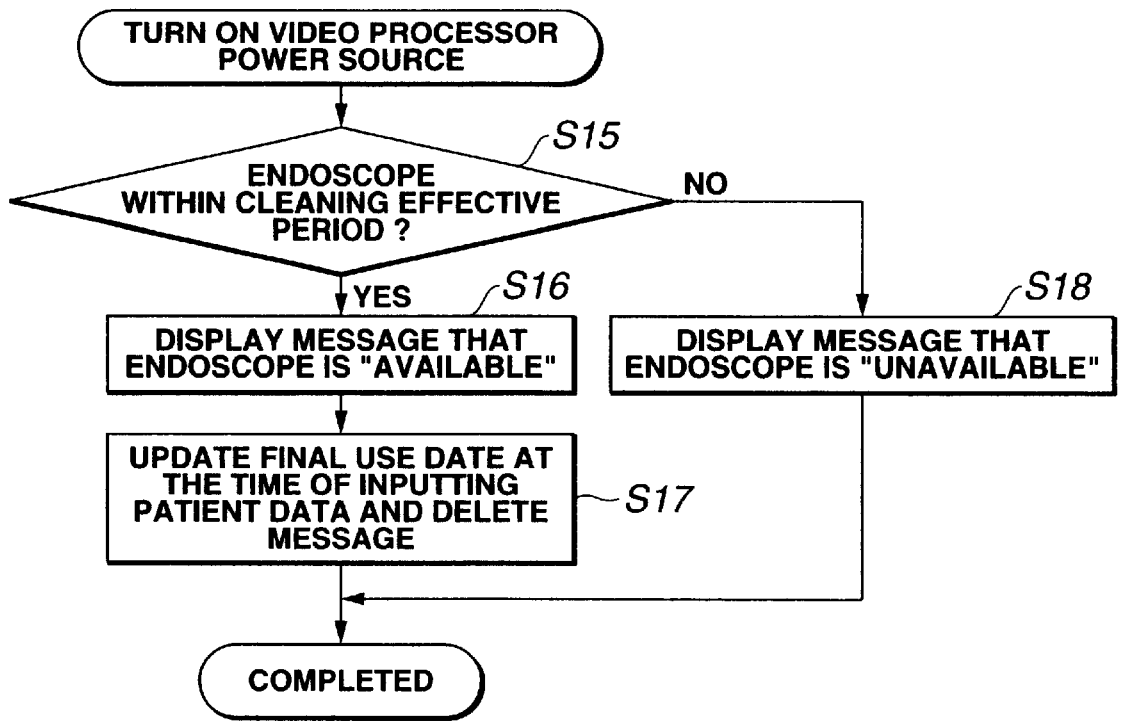

When starting an examination, it may be possible to confirm whether the endoscope 10 is in a sanitary condition with the viewing monitor 12 of the video processor 11. Steps of such confirmation processing are explained hereinafter in conjunction with FIG. 20.

First, the endoscope 10 is connected to the video processor 11. When the power source of the video processor 11 is turned on, processing advances to step S15.

In step S15, the last use day and the last cleaning day acquired from the server 4 are compared with each other so as to judge whether the endoscope 10 is within the sanitary period. If the last use day is after the last cleaning day, the CPU 153 determines that the endoscope 10 is not in a sanitary condition and processing advances to step S18.

Even if the last cleaning day comes after the last use day, if the last use day is not within the effective period recorded in the cleaning condition administration table, the CPU 153 determines that the endoscope 10 is not in a sanitary condition and processing advances to step S18.

If the endoscope is cleaned after the last use day and is within the effective period, the CPU 153 determines that the endoscope 10 is in a sanitary condition and hence, processing advances to step S16.

If the endoscope 10 is in a sanitary condition, the processing advances to step S16 where the endoscope model name and a message "available" are superposed on the viewing monitor 12. When patient data are inputted, the CPU determines that an examination has started. The patient data is assumed to be transferred from the video processor 11 to the server 4 through the image recording and reproducing device 3-*a*. Subsequently, processing advances to step S17.

When patient data are transferred to the server 4 in step S17, the CPU determines that the examination has started. Accordingly, the server 4 reads and records time information administrated by a clock (not shown) provided to the CPU 71 as the last use day and updates the last use day of the endoscope 10 in the cleaning condition administration table corresponding to the set final use day. The updated cleaning condition administration table is recorded in the large capacity hard disc 81. In the video processor 11, the endoscope model name and the message "available, are erased and processing is completed.

When the CPU determines that the endoscope 10 is not in a sanitary condition in step S15, processing advances to step S18 where the video processor 11 superposes the endoscope model name and the message "unavailable" in the viewing monitor 12. When the user performs manipulation by means of the key board 49, the message is erased and processing is completed.

The endoscope 10 is mounted on the video processor 11 just before performing an examination. The endoscope 10 is identified based on the inherent information in the EEPROM 30 of the endoscope 10. Whether the endoscope 10 is available is determined by confirming the sanitary condition of the endoscope 10.

The user may confirm whether the endoscope 10 is available by inputting the expected use date of the endoscope 10 by manipulating the keyboard 142 or the mouse 143 of the examination reservation device 7. When the expected use day is inputted, the sanitary condition administration table is read from the large capacity hard disc 81 and transferred to the examination reservation device 7. If the last cleaning day of the endoscope 10 is after the last use day of the endoscope 10, and the expected use day of the endoscope 10 is within the sanitary period from the last cleaning day, the examination reservation device 7 displays "available" on the PC display 140. If the above conditions are not met, the examination reservation device 7 displays "unavailable-cleaning is necessary" on the PC display 140.

The endoscope use condition administration table, shown in FIG. 13, is recorded in the server 4. If an endoscopic examination is performed with the use of the endoscope 10, the use condition of the endoscope 10 is administrated by using the endoscope use condition administration table. Steps of use condition administration processing are explained in conjunction with FIG. 21.

First, the endoscope 10 is connected to the video processor 11 of the endoscope system 2-a and the power source of the video processor 11 is turned on.

With control performed by the CPU 71, the server 4 reads the file of the endoscope use condition administration table from the large capacity hard disc 81 and preserves the file on the RAM 73.

The endoscope model names and the manufacturing numbers recorded in the endoscope use condition administration table are identical to those recorded in the endoscope administration table shown in FIG. 10. When the endoscope model and manufacturing number are recorded in the endoscope administration table in step S12 of FIG. 19, the endoscope model name and the manufacturing number of the endoscope use condition administration table are simultaneously updated and recorded in the large capacity hard disc 81.

In step S21, with control performed by the CPU 29, data on the model name "G-300" and the manufacturing number "123-45" are read from the EEPROM 30 of the endoscope 10. The read-out data on the model name and the manufacturing number are inputted into the video processor 11 through the I/F 41.

The data shown in FIG. 9A are recorded in the EEPROM 30 of the endoscope 10 at the time of manufacturing the endoscope 10.

When the endoscope model name and the manufacturing number are read, processing advances to step S22. The CPU 42 disposed in the video processor 11 transmits a command to update the number of endoscope extractions and insertions, the endoscope model name and the manufacturing number from the communication I/F 47 to the image recording and reproducing device 3-a.

Upon receiving command to update the number of endoscope extractions and insertions, the endoscope model name and the manufacturing number through the communication I/F 60, the image recording and reproducing device 3-a outputs same on the network 9 through the network I/F 61.

The command to update the number of endoscope extractions and insertions, the endoscope model name and the manufacturing number which are outputted from the image recording and reproducing device 3-a are received by the network I/F 76 of the server 4.

Upon receiving the command to update the number of endoscope extractions and insertions, the endoscope model name and the manufacturing number, the server 4 reads the number of endoscope extractions and insertions of the endoscope use condition administration table based on the endoscope model name "G-300" and the manufacturing number "123-45". The number of endoscope extractions and insertions for this model is "0". One is added to the number so "1" is the updated datum. Upon updating the datum on the number of endoscope extractions and insertions, the server 4 writes the endoscope use condition administration table in the large capacity hard disc 81.

Upon completion of writing the endoscope use condition administration table, processing advances to step S23.

In step S23, processing pauses for the entry of patient data by manipulating the keyboard 49 of the video processor 11. When patient data are inputted, the CPU determines that the examination is started and processing advances to step S24.

In step S24, when patient data are inputted, the patient data are transmitted from the communication I/F 47 of the video processor 11 to the image recording and reproducing device 3-a.

Upon receiving the patient date through the communication I/F 60, the image recording and reproducing device 3-a outputs the patient data on the network 9 through the network I/F 61.

The patient data outputted from the image recording and reproducing device 3-a are received by the network I/F 76 of the server 4.

Upon receiving the patient data, the server 4 determines that an examination has started and reads the corresponding number of examinations from the endoscope use condition administration table based on the endoscope model name "G-300" and the manufacturing number "123-45" which are received in advance. In this example, the number of examinations is "0". One is added to the number so that "1" is the updated datum. The server 4 writes the endoscope use condition administration table which has updated the datum on the number of examinations in the large capacity hard disc 81.

When the patient data is inputted, the server 4 determines that the examination has started and acquires and records the current time from time information administrated by a clock (not shown) provided to the CPU 71 as the examination start time in the RAM 73.

Subsequently, processing advances to step S25. In step S25, when the release switch 28 of the endoscope 10 is pushed down, the CPU determines that a release signal is present. When the release signal is inputted, the image recording and reproducing device 3-a freezes images inputted to the frame memory 56 and records the images. The number of times that the release switch is pushed is measured as one of parameters for measuring the use frequency or the endoscope.

When the release switch 28 is pushed down, processing advances to step S26. The pushing down of the release switch is detected by the CPU 29 and a release signal is outputted from the I/F 31. The release signal is inputted from the I/F 41 to the video processor 11.

The endoscope model end the manufacturing number are read the RAM 44 of the video processor 11 and the EEPROM 30 and outputted from the communication I/F 47 together with the notification of detection of the release signal.

The notification of detection of the release signal and the data on the endoscope model and the manufacturing number are received through the communication I/F 60 of the image recording and reproducing device 3-a. These data are outputted on the network 9 through the network I/F 61 of the image recording and reproducing device 3-a.

The notification of detection of the release signal and the data on the endoscope model and the manufacturing number outputted on the network 9 are received by the network I/F 76 of the server 4. Upon receiving these data, the server 4 updates the number of releases in the endoscope use condition administration table and writes the updated number of releases in the large capacity hard disc 81.

When the number of releases is updated, the processing advances to step S27. At step S27 the CPU determines whether an examination completion command is inputted by manipulating the keyboard 49.

If the examination completion command is not inputted, processing moves to step S25 and returns to the processing for determining whether the previously mentioned release switch 28 is pushed down.

If the examination completion command is inputted by manipulating the keyboard 49, processing advances to step S28, where the examination completion command is outputted from the communication I/F 47 of the video processor 11 to the image recording and reproducing device 3-a.

When the examination completion command is inputted, the image recording and reproducing device 3-a performs examination completion processing. The examination completion processing closes what has been built on the patient data on the examination and the examination images and the like which have been inputted and transfers to the server and records in the large capacity hard disc 81 patient data and examination images which have not yet been transferred to the server 4 in the image recording and reproducing device 3-a.

At the time of performing examination completion processing, the examination completion command is also transferred from the image recording and reproducing device 3-a to the server 4. When the examination completion command is transferred to the server 4, the CPU 71 of the server 4 reads and sets the time of a clock incorporated in the CPU 71 as the exam nation completion time.

The examination start time is stored in the RAM 73 in step S24. The CPU 71 reads this examination start time and calculates the difference between the examination start time and the examination completion time. This calculated time is set as the examination time. The examination time is substantially regarded as the use time. Then, the examination time is added to the accumulated use time of the endoscope use condition administration table. The updated endoscope use condition administration table is recorded in the large capacity hard disc 81.

Figure 21:
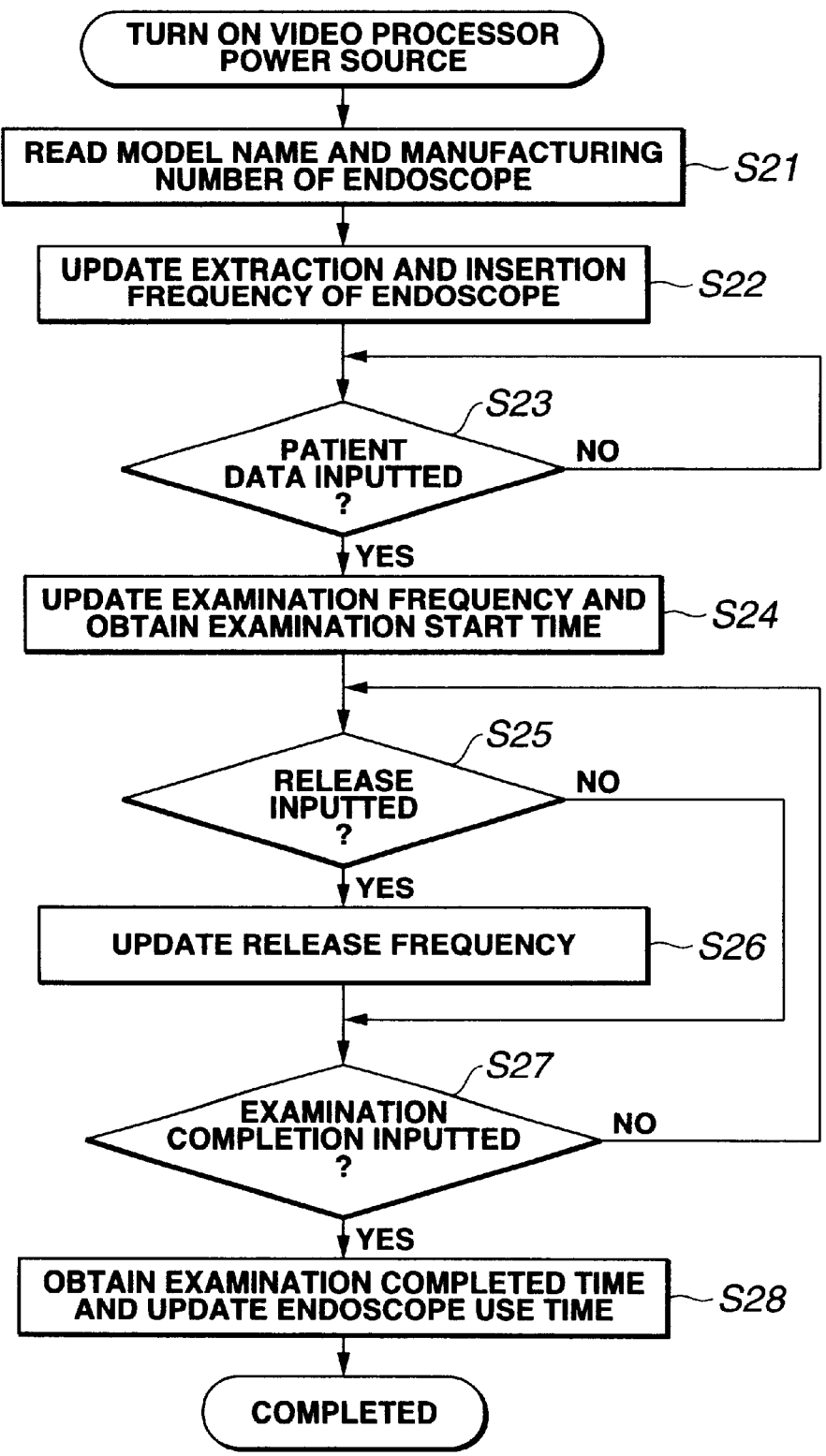

Although the same endoscope 10 is used throughout a single endoscopic examination, the endoscope may be exchanged during an examination. In such a case, processing ranging from step S21 to step S28 is stopped in the midst of the processing. When the endoscope 10 is exchanged, the processing of FIG. 21 is initiated. However, since the inputted patient data are preserved in the RAM 44 in the video processor 11 and displayed on the viewing monitor 12 even after the endoscope 10 is exchanged, it is unnecessary to input the patient data by manipulating the keyboard 49 again. In this case, processing may skip step 23.

During examination, the endoscope use condition window shown in FIG. 14 can be confirmed on the PC display 140 of the examination reservation device 7. The administration number or the manufacturing number of the endoscope 10 which is connected to the endoscope system 2-a to 2-c or the endoscope cleaning device 8 is sent to the server 4. The administration number or the manufacturing number is also sent to the examination reservation device 7. The recommended maintenance period is also transmitted simultaneously.

With respect to the recommended maintenance period, the maximum number of examinations, the maximum number of endoscope extractions and insertions, the maximum number of releases and the maximum accumulated use time until maintenance are set for every endoscope 10. The fastest period which reaches any one of these values is calculated.

As shown in FIG. 13, the No. 5 endoscope 10 has a long accumulated use time compared to the number of examinations, the number of endoscope extractions and insertions and the number of releases thereof, for example, the accumulated use time is considered to be the fastest one which will reach the maximum accumulated use time. Based on the use start date "1998/9/11", the date "1999/4/2" which is acquired from the server 4 and the present accumulated use time "6240 H" of the No.5 endoscope 10, the date "1999/8" on which the maximum accumulated time reaches "10000 H" is calculated and displayed.

The endoscope 10 irradiates light which the lighting source lamp 16 supplies to a viewing portion from the distal end portion of the insertion part 22 through the connector 15, the manipulation part 21 and the insertion part 22. The CCD 26 arranged at the distal end portion 23 of the insertion part 22 converts the irradiated image of the viewing portion into electric signals and transmits the signals to the video processor 11 through the connector 15.

The video processor 11 converts the electric signals to video signals which are transmitted to a viewing monitor 12 through a cable 38. The viewing monitor 12 displays the images real time. Simultaneous with such processing, the video processor 11 transmits video signals to the image recording and reproducing device 3-a.

During an examination, the CPU 42 monitors the connection of the endoscope 10 through the I/F 41. When the endoscope 10 is extracted or inserted, this extraction or insertion event is transmitted to the image recording and reproducing device 3-a.

When the release switch 28 provided to the manipulation part 21 is manipulated, a release commend is transmitted to the image recording and reproducing device 3-a. Upon receiving the release command, the image recording and reproducing device 3-a records the endoscopic images, as explained later.

Upon completion of recording of images, by manipulating input means of the keyboard 49, the completion of examination is indicated to the video processor 11. Upon receiving the indication of the completion of examination, the video processor 11 transmits an examination completion command to the Image recording and reproducing device 3-a.

Subsequently, the image recording and reproducing device 3-a records the endoscopic image obtained by the video processor 11. First, the patient information transmitted from the video processor 11 are inputted through the communication I/F 60 of the image recording and reproducing device 3-a and transmitted to and recorded in the herd disc 63 or the server 4 through the network I/F 61. In the server 4, the inputted patient information and the administration number of the endoscope 10, which are inputted simultaneously with the inputted patient information, are correlated and registered in the patient information data base of the large capacity hard disc 81.

Figure 22:
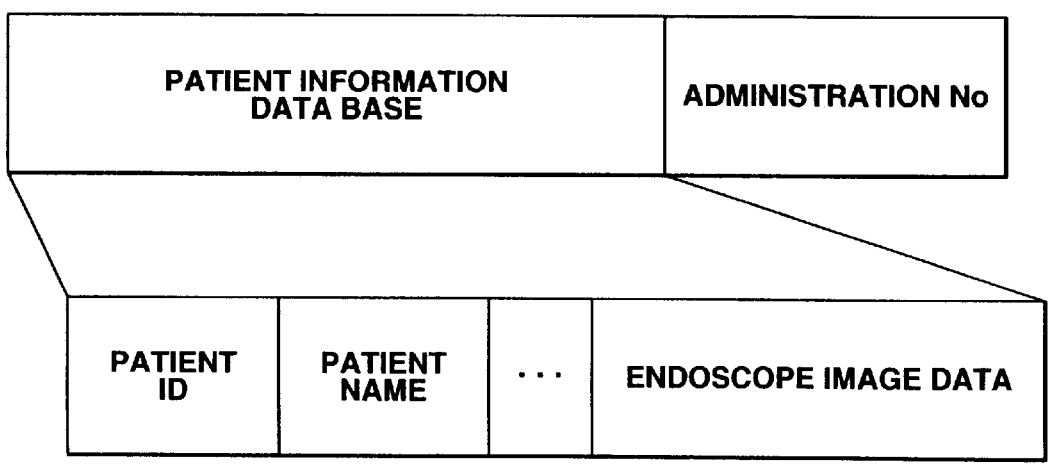

FIG. 22 shows the patient information data base or the large capacity hard disc 81. As shown in FIG. 22, the patient information is recorded in the patient information data base correlated with the administration number of the endoscope 10. In FIG. 22, when the administration number is 1, for example, as understood from FIG. 10, the endoscope 10 has a model name is C-250 and a manufacturing number 000-11. Although the endoscopes 10 are simply indicated by the administration number in FIG. 22, the model names and the manufacturing numbers or the like may be displayed simultaneously, as shown in FIG. 10.

In this manner, in the large capacity hard disc 81, together with the endoscope image data, the identification information or the like of the endoscopes 10 which are used for obtaining endoscopic image data are recorded and correlated with the endoscope data. Accordingly, the preparation of the examination result report, shown in FIG. 15, explained later can be facilitated. That is, since the patient information data base and the information on the endoscope or the like which is used for obtaining images of the patient are centrally administrated by the large capacity hard disc 81 and correlated, the examination result report can be prepared easily.

The video signals transmitted from the video processor 11 are converted to digital signals by the A/D converter 51 and recorded in the frame memory 56. Upon receiving the release command transmitted from the video processor 11 through the communication I/F 60, the frame memory 56 transmits the video signals recorded in the frame memory 56 to the image compression and expansion part 58, where image compression processing is performed.

During image compression processing, three kinds of compression images, that is, reversible compression images, with a compression rate of ½ to ⅓, irreversible compression images, with a compression rate of approximately 1/10, and index images, of irreversible compression, are prepared. The reversible compression images and the irreversible compression images record the endoscopic images such that respective reproduced images are the same.

The index images are produced by cutting portions of the endoscopic images and subjecting same to shrinking processing. The index images are displayed on a list for selecting the endoscopic images, as explained later. These three kinds of compression images are transmitted to the hard disc 63 or the server 4 through the network I/F 61 where they are correlated with appropriate patient information in the data base which have been recorded preliminarily and are recorded for every one examination unit.

When an examination is completed end the video processor 11 transmits the examination completion command, which indicates that the examination is completed to the image recording and reproducing device 3-*a*, the examination completion command is inputted through the communication I/F 60 and transmitted to the CPU 53. Upon receiving the examination completion command, the CPU53 stops the processing with respect to the examination and indicates the completion of the examination to the server 4.

During an endoscopic examination, the number of extractions and insertions of the endoscope 10 and the number of releases are counted in the image recording and reproducing device 3-*a*. When the examination completion command, which initiates measurement of the examination time, is inputted to the image recording and reproducing device 3-*a*, the number of extractions and insertions of the endoscope 10, the number of releases and the examination time are transmitted to the server 4 with the endoscope administration number or the manufacturing number.

For example, if "No. 1" endoscope 10 is used, the corresponding last use day in the table of FIG. 12 is updated to "1999/4/2" or whichever date the endoscope was last used. Based on the data which the CPU 71 has received, the server 4 updates the number of extractions and insertions, the number of releases and the accumulated use time in the endoscope use condition administration table shown in the table of FIG. 13.

Upon completion of an endoscopic examination, the endoscope 10 is connected to the endoscope cleaning device 8 so as to perform cleaning. The CPU 153 of the endoscope clearing device 8 communicates with the connected endoscope 10 through the I/F 152 and acquires the administration number or the manufacturing number of the endoscope 10 from the EEPROM 30. Subsequently, the cleaning control part 160 cleans the endoscope 10.

Upon completion of cleaning, the completion of cleaning is indicated to the server 4 with the administration number or the manufacturing number of the endoscope 10. The server 4 updates the last cleaning day of the corresponding endoscope 10 shown in the table of FIG. 12 to "1999/4/2", or the date on which cleaning is completed.

Subsequently, reproducing the endoscopic images with the image reproducing device 6 after completion of an examination occurs. The user selects the examination to be reproduced by the image reproducing device 6. The selection of the examination is performed based on information such as the name of a patient, the patient ID, the examination day and time, the contents of an examination or the like.

When retrieving based on the examination day and time, a group of examinations in which a desired examination falls are displayed on the viewing monitor 12. The year, month and day on which a given examination was performed are inputted to the image reproducing device 6 by means of the key board 127 or the mouse 128, then examinations performed on the inputted day are displayed. Alternatively, examinations performed within the preceding are displayed. Examinations performed within the previous month also may be displayed. Then, the corresponding examination is selected by the manipulation of the keyboard 127 or the mouse 128.

When retrieving examination information based on patient ID numbers, when the patient ID number is inputted, all of the examinations of the patient having that ID number are displayed on the PC display 123.

From these examinations, the corresponding examination is selected based on the information, such as the examination day and time, the content of an examination or the like, with the manipulation of the keyboard 127 or the mouse 128.

Retrieval may be performed according to patient names, patient ID numbers, examination days, contents of examinations and the like which are combined arbitrarily and then narrowed down.

With respect to the same patient, if examinations occurring on the same examination day are present, the examination can be selected by selecting the kind of the examination, that is, "upper part" or "lower part" or the name of doctor.

Upon specifying the corresponding examinations, the index images of the examinations are displayed on the viewing monitor 125. The index images are read from the server 4 or the optical disc device 102 of the image recording device 5. The image reproducing device 6 receives the index images through the network I/F 119. The received index images are subjected to image expansion processing in the image expansion part 117. Subsequently, the expanded index images are written in the frame memory 115 by means of the frame memory controller 116 and displayed on the viewing monitor 125.

The user selects a given image from the index images displayed by means of the keyboard 127 or the mouse 128.

A reversible compression image or an irreversible compression image which corresponds to the selected index image is read from the server 4 or the optical disc device 102 in the same manner as the index images and displayed on the viewing monitor 125 in an enlarged format.

The image reproducing device 6 may read and display the patient information data base with the images from the server 4 as an examination result report, as shown in FIG. 15. As shown in the examination reservation window of FIG. 11, where the examination "patient ID : 000001" is performed twice on "1999/4/2", the narrowing down of examination data to select is performed based on the examination date and the kinds of examinations.

For example, an examination which uses "endoscope model C-250" is associated with an examination of the "upper part". By selecting "upper part" as the examination type with the manipulation of the keyboard 127 or the mouse 128, the examination can be selected. Simultaneously, "endoscope used: C-250" is automatically inputted in the examination result report of FIG. 15. When the cursor is moved to the application site of the examination result report, application sites, such as "gullet", "stomach", "duodenum", "large intestine", "gullet", and "stomach", which are associated with endoscope models are displayed on the examination result report. When "stomach" is selected, the data are fixed.

With respect to doctors in charge of examinations, from "Sato", "Ishida", "Ohta", "Yamada", only "Sato" and "Ishida" which are associated with endoscope models are displayed, thus selection becomes possible among displayed names of doctors. In this example, selected data are transmitted to the server 4 and registered in the patient information data base in the large capacity hard disc 81.

The images which are recorded in the server 4 are sequentially and automatically backed up by the image recording device 5, for example, once a day at midnight, when examinations are not performed. Due to such a backup operation, with respect to examinations performed on a day, four kinds of data on the patient information, the reversible compression images, the irreversible compression images and the index images, which are recorded in the server 4, are copied to the optical disc device 102 connected to the image recording device 5.

However, taking into account the capacity of the optical disc device 102, the user may choose whether to back up reversible compression images. The information copied to the optical disc device 102 is preserved without being erased. By increasing the number of optical disc devices 102, the present invention can accommodate an increasing number of examinations. Nonetheless, to prevent the recording data storage from reaching the upper limit, older information may be erased.

Where a plurality of optical discs are provided, a specific examination is selected and recorded in a specific optical disc. The data from one examination may be stored on an optical disc labeled "disc No. 1". Data from other examinations are sequentially recorded in the disc No. 2 and the succeeding discs.

The examination designation table for designating each examination is shown in a table of FIG. 16.

This table is recorded in the large capacity hard disc 81 of the server 4. The table can be read to the image reproducing device 6 and displayed and edited on the PC display 123. At the time of recording the table in the optical disc device 102, the data in the table and the patient information data base in the large capacity hard disc 81 are compared. For example, data with "patient ID : 000001" and "disease name : gastric cancer" are recorded in disc No. 1. When "disease name : gastric cancer" is inputted in the examination result report of FIG. 15, the examination data are recorded in the disc No. 1.

When retrieving images with the image reproducing device 6, first, a collation is performed on the examination designation table. As a result, if images which correspond to "disc No. 1" are present, the retrieval of the images can be performed at a high speed. By giving priority over mounting of the specific optical disc "disc No. 1" set here to an optical disc drive (not shown) of the optical disc device 102, the higher reading and writing of the designated examination images can be realized.

This embodiment has the following effects or advantages.

In this embodiment, every endoscope is given inherent information and is centrally administrated. Thus, the present use condition, the past use history, the repair history, the cleaning history and the like of the endoscope can be totally administrated.

Whether the endoscope which is to be used for the endoscope examination is clean and available can be easily ascertained.

Maintenance time can be understood based on the past use condition of every endoscope thus, endoscopic examination can be carried out smoothly.

The endoscope which is used in an examination can be instantly recognized which is also effective for carrying out endoscopic examination.

By correlating types of endoscopes and examinations, and by identifying an endoscope used in an examination, information administration in an examination becomes easy. At the time of preparing a report after performing an examination, the endoscope and the examination data are linked and hence, the selection of the examination data becomes easy. The data can be narrowed down for every kind of endoscope, thus preparation of a report can be performed smoothly.

At the time of recording images after performing an examination, only the specific examination can be selected with the use of keywords. The images can be preserved in an optical disc thus, the retrieval can be performed at a high speed and smoothly at the time of extracting the specific images and performing the retrieval.

Not only may registration be completed before connecting the endoscope to the endoscope image filing system, but the registration can be automatically performed from the endoscope image filing system thus, the erroneous data inputting can be prevented with minimal time and effort.

Figure 23:
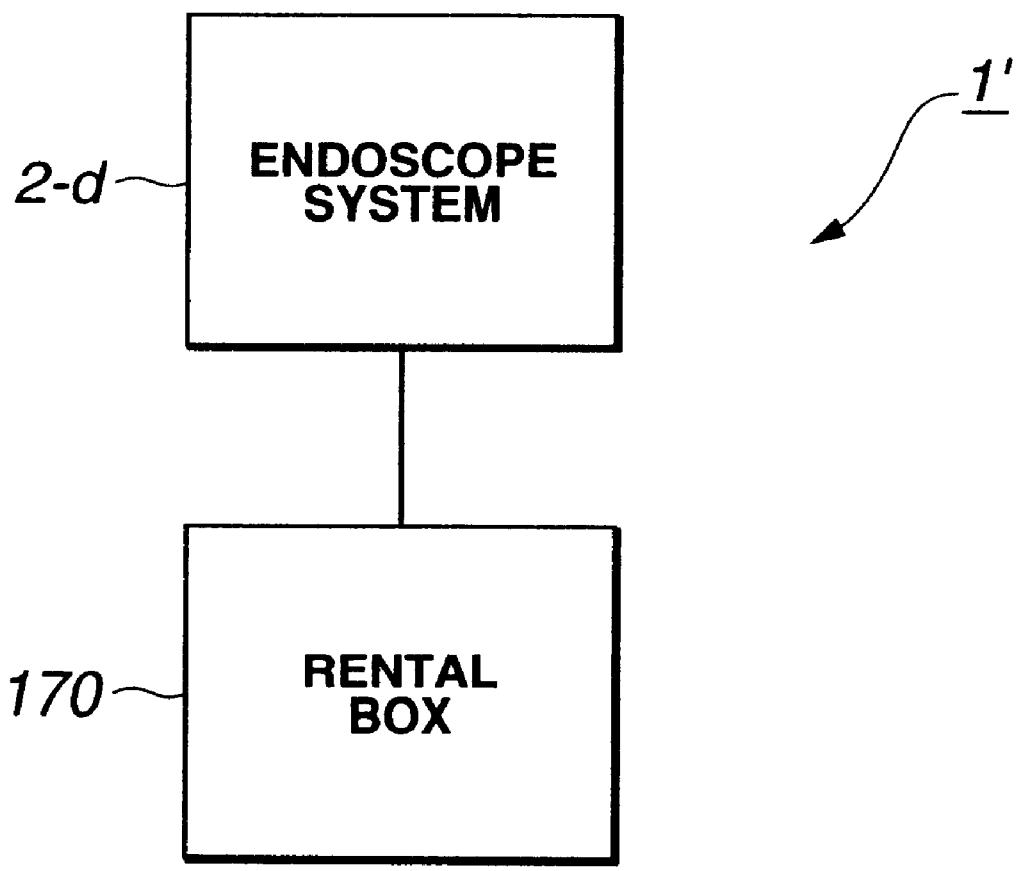

A second embodiment of the present invention is explained in conjunction with FIG. 23 and FIG. 24. In this embodiment, the endoscope system and a rental box are combined. The use frequency of the endoscope is ascertained when the endoscope is rented or the like. The use frequency is used as the administration information for performing the corresponding maintenance such as repair and exchange.

FIG. 23 is a schematic view of the endoscope image filing system 1'. FIG. 24 is a block diagram showing the constitution of a rental box 170.

The endoscope image filing system 1' is comprised of an endoscope system 2-*d* and the rental box 170 which is used while connected to the endoscope system 2-*d*. The endoscope system 2-*d* is similar to the endoscope system 2-*a* to 2-*c* shown in FIG. 1 and hence, the explanation thereof is omitted.

As shown in FIG. 24, since the rental box 170 does not use a network, the network I/F 61 is omitted from the image recording and reproducing device 3-a shown in FIG. 3.

Instead, the rental box 170 includes an A/D converter 171 which receives standard video signals transmitted from the video output terminal of the video processor 11 and performs an A/D conversion of the video signals, a D/A converter 172 which performs a D/A conversion of digital video signals, a CPU 173, a ROM 174, a RAM 175, a frame memory 176, a frame memory controller 177, an image compression and expansion part 178, a hard disc controller 179, a communication I/F 180, which are connected to a bus 181, and a hard disc 182, which is connected to the hard disc controller 179.

As mentioned above, since the network I/F 61 is omitted from the image recording and reproducing device 3-a shown in FIG. 3, except for the operation performed through the network, the rental box 170 has the same functions as the image recording and reproducing device 3-a shown in FIG. 3 thus, explanation of these functions is omitted.

The endoscope use condition administration table shown in FIG. 13 is recorded in the rental box 170. In performing an endoscopic examination with the endoscope 10, the use condition of the endoscope 10 is administrated by employing this endoscope use condition administration table. This use condition administration step is explained in conjunction with FIG. 22.

The endoscope 10 is connected to the video processor 11 of the endoscope system 2-d and the power source of the video processor 11 is turned on.

With control performed by the CPU 173, the rental box 170 reads and saves the file of the endoscope use condition administration table from the hard disc 182 to the file on the RAM 175.

The step for recording the endoscope model name and the manufacturing number in the endoscope use condition administration table is identical to the step for recording them in the endoscope use condition administration table of the server 4. When using the endoscope 10 for the first time, the endoscope model name and the manufacturing number of the endoscope use condition administration table are simultaneously updated and recorded in the hard disc 182.

In initial step S21, with control performed by the CPU 29, the data on the model name "G-300" and the manufacturing number "123-45" are read by the EEPROM 30 of the endoscope 10. The read-out data on the endoscope model name and the manufacturing number are inputted into the video processor 11 through the I/F 41.

The data shown in FIG. 9A are recorded in the EEPROM 30 of the endoscope 10 at the time of manufacturing.

When the endoscope model name and the manufacturing number are read, processing advances to step S22. The CPU 42 disposed in the video processor 11 transmits a command to update the number of endoscope extractions and insertions, the endoscope model name and the manufacturing number from the communication I/F 47 to the rental box 170.

Upon receiving the command to update the number of endoscope extractions and insertions, the endoscope model name and the manufacturing number through the communication I/F 180 of the rental box 170, the rental box 170 reads the number of endoscope extractions and insertions of the endoscope use condition administration table from the endoscope model name "G-300" and the manufacturing number "123-45". In this example, the number of endoscope extractions and insertions is "0". One is added so that "1" becomes the updated datum. Upon updating the datum on the number of endoscope extractions and insertions, the rental box 170 writes the endoscope use condition administration table in the hard disc 182.

Upon completion of writing of the endoscope use condition administration table, the processing advances to step S23.

In step S23, the processing pauses for the entry of patient data by manipulating the keyboard 49 of the video processor 11. When the patient data are inputted, the CPU determines that an examination is started and the processing advances to step S24.

In step S24, when the patient data are inputted, the patient data are transmitted from the communication I/F 47 of the video processor 11 to the communication I/F 180 of the rental box 170.

Upon receiving the patient data, the rental box 170 determines that an examination has started and reads the corresponding number of examinations from the endoscope use condition administration table based on the endoscope model name "G-300" and the manufacturing number "123-45", which were received in advance. In this example, the number of examinations is "0". One is added and becomes the updated datum. The rental box 170 writes the endoscope use condition administration table, including the updated datum, on the number of examinations in the hard disc 182.

When patient data are inputted, the rental box 170 determines that an examination has started and acquires the time from time information administrated by a clock (not shown) provided to the CPU 173, which is preserved as the examination start time, in the RAM 115.

Subsequently, processing advances to step S25. In step S25, when the release switch 28 of the endoscope 10 is pushed down, a release signal is inputted. When the release signal is inputted, the rental box 170 freezes images inputted into the frame memory 176 and records the images. The number of times that the release switch is pushed is measured as one of the parameters for measuring the use frequency of the endoscope 10.

When the release switch 28 is pushed down, processing advances to step S26. When pushing down of the release switch 28 is detected by the CPU 29, a release signal is outputted from the I/F 31. The release signal is inputted through the I/F 41 to the video processor 11.

The endoscope model and the manufacturing number are read from the RAM 44 of the video processor 11 from the EEPROM 30, which are outputted from the communication I/F 47 with the notification of detection of the release signal.

The notification of detection of the release signal and the data on the endoscope model and the manufacturing number are received through the communication I/F 180 of the rental box 170. Upon receiving these data, the rental box 170 updates the number of releases in the endoscope use condition administration table and writes the updated number of releases in the hard disc 182. When the number of releases is updated, processing advances to step S27.

At step S27, the CPU determines whether an examination completion command is inputted by manipulating the keyboard 49.

If an examination completion command is not inputted, processing moves to step S25 and returns to the processing for determining whether the previously mentioned release switch 28 is pushed down.

If the examination completion command is inputted by manipulating the keyboard 49, processing advances to step S28, where an examination completion command is outputted from the communication I/F 47 of the video processor 11 to the communication I/F 180 of the rental box 170.

When the examination completion command is inputted, the rental box 170 performs examination completion processing. The examination completion processing closes and records what has been built on the patient data on an examination and the examination images and the like which have been inputted as a data base in the hard disc 182.

During examination completion processing, the CPU 173 of the rental box 170 also reads the time from a clock incorporated in the CPU 173, which is set as the examination completion time.

The examination start time is stored in the RAM 175 in step S24. The CPU 173 reads this examination start time and calculates the difference between the examination start time and the examination completion time. This calculated time is set as the examination time. The examination time is substantially regarded as the use time. Then, the examination time is added to the accumulated use time of the endoscope use condition administration table, which is recorded in the hard disc 182.

Although the same endoscope 10 is used throughout an endoscopic examination, the endoscope 10 may be exchanged in the midst of the examination. In such a case, processing from step S21 to step S28 is stopped in the midst of the processing. When the endoscope 10 is exchanged, processing of FIG. 21 is performed from the beginning. However, since the inputted patient data are preserved in the RAM 44 in the video processor 11 and displayed on the viewing monitor 12 even after the endoscope 10 is exchanged, it is unnecessary to input patient data by manipulating the keyboard 49 again. Thus, processing may be performed while skipping the step 23.

Although the images obtained by the endoscope are recorded with the use frequency of the endoscope, the rental box 170 may be constituted such that the recording of the images is not performed by the rental box 170 and only the recording of use frequency is performed. In this case, the A/D converter 171, the D/A converter 172, the frame memory 176, the frame memory controller 177 and the image compression and expansion part 178 can be omitted. Further, the recording of large amounts of data becomes unnecessary thus, a nonvolatile memory, such as a flash memory, can be used in place of the hard disc 182.

According to this embodiment, even when endoscopes are rented, the use frequency can be ascertained and maintenance and the like can be performed properly with the use of the administration information provided for maintenance or the like.

In the present invention, it is apparent that working modes different in a wide range can be formed on the basis of the present invention without departing from the spirit and the scope of the invention. The present invention is not restricted by any specific embodiments except being limited by the appended claims.

What is claimed is:

1. A data filing system for an endoscope comprising:
   a first endoscope adapted to be insertable in a body to be inspected,
   a first identification information outputting device provided to said endoscope for outputting identification information necessary for identifying said first endoscope,
   a first inherent information generating device for generating inherent information on a use condition inherent to said first endoscope, and
   a memory device for storing endoscopic image data obtained through said first endoscope, said identification information outputted by said first identification information outputting device and said inherent information generated by said first inherent information generating device while setting correspondence between these data and information.

2. A data filing system for an endoscope according to claim 1, further comprising:
   a second endoscope, including:
      a second identification information outputting device which outputs second identification information for identifying said second endoscope; and
      a second inherent information generating device which generates inherent information on inherent use conditions of said second endoscope.

3. A data filing system for an endoscope according to claim 2, wherein said memory device stores first and second endoscope image data respectively obtained through said first and second endoscopes, said first and second identification information respectively outputted by said first and second identification information outputting devices and said first and second inherent information respectively generated by said first and second inherent information generating devices while setting correspondence among said data and information.

4. A data filing system for an endoscope according to claim 2, wherein said memory device is connected to said first and second identification information outputting devices and said first and second inherent information generating devices through a network device.

5. A data filing system for an endoscope according to claim 2, wherein said first and second identification information outputting devices and said first and second inherent information generating devices are respectively constituted by first and second non-volatile memories.

6. A data filing method for endoscope comprising:
   outputting identification information for identifying an endoscope,
   generating inherent information on a use condition inherent to the endoscope, and
   storing endoscopic image data obtained through the endoscope, the identification information, and the inherent information while setting correspondence among the respective data and information.

7. A data filing system for an endoscope comprising:
   a first endoscope adapted to be insertable in a body to be inspected,
   a first identification information outputting devices produced to said endoscope for outputting identification information necessary for identifying said first endoscope,
   a first inherent information generating device for generating inherent information on cleaning inherent to said first endoscope, and
   a memory device for storing endoscopic image data obtained through said first endoscope, said identification information outputted by said first identification information outputting device and said inherent information generated by said first inherent information generating device while setting correspondence among said data and information.

8. A data filing system for an endoscope according to claim 7, further comprising:
   a second endoscope, including:
      a second identification information outputting device which outputs second identification information for identifying said second endoscope; and a second inherent information generating device which generates inherent information on inherent cleaning of said second endoscope.

9. A data filing system for an endoscope according to claim 8, wherein said memory device stores first and second endoscope image data respectively obtained through said first and second endoscopes, said first and second identification information respectively outputted by said first and second identification information outputting devices and said first and second inherent information respectively generated by said first and second inherent information generating devices while setting correspondence among said data and information.

10. A data filing system for an endoscope according to claim 8, wherein said memory device is connected to said first and second identification information outputting devices and said first and second inherent information generating devices through a network device.

11. A data filing method for an endoscope comprising:
outputting identification information for identifying an endoscope,
generating inherent information on cleaning inherent to the endoscope, and
storing endoscopic image data obtained through the endoscope, the identification information, and the inherent information while setting correspondence among the data and information.

12. A data filing system for an endoscope comprising:
a first endoscope adapted to be insertable in the a body to be inspected,
a first identification information outputting device provided to said first endoscope for outputting first identification information necessary for identifying said first endoscope,
a first inherent information generating device for generating first inherent information on use frequency inherent to said first endoscope, and
a memory device for storing endoscopic image data obtained through said first endoscope, said first identification information outputted by said first identification information outputting device and said first inherent information generated by said first inherent information generating device while setting correspondence among said data and information.

13. A data filing system for an endoscope according to claim 12, further comprising:
a second endoscope, including:
a second identification information outputting device which outputs second identification information for identifying said second endoscope; and
a second inherent information generating device which generates inherent information on inherent use frequencies of said second endoscope.

14. A data filing system for an endoscope according to claim 13, wherein said memory device stores first and second endoscope image data respectively obtained through said first and second endoscopes, said first and second identification information respectively outputted by said first and second identification information outputting devices and said first and second inherent information respectively generated by said first and second inherent information generating devices while setting correspondence among said data and information.

15. A data filing system for an endoscope according to claim 13, wherein said memory device is connected to said first and second identification information outputting devices and said first and second inherent information generating devices through a network device.

16. A data filing method for an endoscope comprising:
outputting identification information for identifying an endoscope,
generating inherent information on use frequency inherent to the endoscope, and
storing endoscopic image data obtained through the endoscope, the identification information, and the inherent information while setting correspondence among the data and information.

17. A data filing system for an endoscope comprising:
a plurality of endoscopes,
memory devices provided to each of said respective endoscopes for preserving inherent information unique for every endoscope,
an image inputting device which obtains said inherent information from each of said respective endoscopes and inputs endoscopic images or examination data,
a cleaning device which cleans said respective endoscopes and obtains a cleaning result of said endoscopes as well as said inherent information, and
a data recording device to which at least one of said image inputting device and said cleaning device is connected, said data recording device recording said inherent information for each of said endoscopes and endoscopic examination data or cleaning result data while correlating said information and data.

18. A data filing system for an endoscope according to claim 17, further comprising a display device which ascertains which of said endoscopes is in service based on peculiar information of said endoscopes used in combination in said image inputting device and displays said endoscope in service.

19. A data filing system for an endoscope according to claim 17, further comprising a data recording device which counts, records and administrates at least one of a number of examinations, a number of mounting and dismounting of said endoscope to said image inputting device and a number of image recording instruction instructions as use frequency of said endoscopes for each of said endoscopes.

20. A data filing system for an endoscope according to claim 17, further comprising a data calculating device which calculates a lifetime or the maintenance time of each of said endoscopes based on the use frequency of each of said endoscopes.

21. A data filing system for an endoscope according to claim 17, further comprising a data inputting device which inputs examination data including kinds of examination by said endoscopes and a recording device which records said examination data, endoscopic images and endoscopes used in examinations in a correlated manner by correlating said endoscopes and said kinds of examinations.

22. A data filing system for an endoscope according to claim 17, further comprising a data inputting device which narrows down data related with endoscopic examinations depending on kinds of examinations by correlating said endoscopes and said kinds of examinations and performs data inputting.

23. A data filing system for an endoscope according to claim 17, further comprising a cleaning condition determining device which confirms a cleaning result for every endoscope and determines whether said endoscope is clean.

24. A data filing system for an endoscope according to claim 23, further comprising an endoscope use date acquiring device which acquires an endoscope examination date and an endoscope cleaning date, a setting device which sets a cleaning effective period which maintains the cleanliness after cleaning said endoscope, and a cleaning condition determining device which determines a cleaning condition of said endoscope based on said endoscope examination date, said endoscope cleaning date and said cleaning effective period.

25. A data filing system for an endoscope according to claim 17, further comprising reading devices which are provided to every endoscope for reading inherent information which are unique for every endoscope and a writing device which performs writing of inherent information for every endoscope if that inherent information is not written as a result of reading by said reading device.

* * * * *